US010854103B2

(12) United States Patent
O'Dowd et al.

(10) Patent No.: US 10,854,103 B2
(45) Date of Patent: Dec. 1, 2020

(54) MODULAR WEARABLE DEVICE FOR CONVEYING AFFECTIVE STATE

(71) Applicant: Microsoft Technology Licensing, LLC, Redmond, WA (US)

(72) Inventors: Chris O'Dowd, Redmond, WA (US); Asta Roseway, Redmond, WA (US); Mary Czerwinski, Redmond, WA (US); Meredith Morris, Redmond, WA (US); Michele A. Williams, Windsor Mill, MD (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 292 days.

(21) Appl. No.: 15/905,582

(22) Filed: Feb. 26, 2018

(65) Prior Publication Data
US 2018/0182259 A1 Jun. 28, 2018

Related U.S. Application Data

(62) Division of application No. 14/534,581, filed on Nov. 6, 2014, now Pat. No. 9,934,697.

(51) Int. Cl.
*G09B 19/00* (2006.01)
*G06F 3/01* (2006.01)
(Continued)

(52) U.S. Cl.
CPC .............. *G09B 19/00* (2013.01); *A41D 1/04* (2013.01); *A41D 23/00* (2013.01); *A41F 9/00* (2013.01);
(Continued)

(58) Field of Classification Search
CPC .......... G06F 1/163; G06F 3/011; G06F 3/016; G06F 2203/011; G09B 19/00;
(Continued)

(56) References Cited

U.S. PATENT DOCUMENTS

| 8,228,202 B2 | 7/2012 | Buchner et al. |
| 2004/0215958 A1 | 10/2004 | Ellis |

(Continued)

FOREIGN PATENT DOCUMENTS

| CN | 101341458 A | 1/2009 |
| CN | 102016759 A | 4/2011 |

(Continued)

OTHER PUBLICATIONS

"Office Action Issued in European Patent Application No. 15802234.3", dated May 28, 2019, 6 Pages.

(Continued)

*Primary Examiner* — Jerry-Daryl Fletcher
(74) *Attorney, Agent, or Firm* — Alleman Hall Creasman & Tuttle LLP

(57) ABSTRACT

A wearable device conveys information to a user. The device includes a master soft circuit cell and a plurality of actuation soft circuit cells. These cells are physically interconnected to form a garment that is worn by a user and each of these cells includes an electrically non-conductive fabric covering. Each of the actuation cells is electrically connected to and operates under the control of the master cell. The master cell is configured to wirelessly receive actuation instructions and activate a combination of the actuation cells based on the received actuation instructions. Each of the actuation cells is configured to generate a particular actuation that is perceived by one or more senses of the user whenever the actuation cell is activated by the master cell. A system also conveys affective state information to a user.

26 Claims, 11 Drawing Sheets

(51) Int. Cl.

| | |
|---|---|
| G06F 1/16 | (2006.01) |
| A41D 1/04 | (2006.01) |
| A41D 23/00 | (2006.01) |
| A41F 9/00 | (2006.01) |
| A61B 5/16 | (2006.01) |
| G08B 7/02 | (2006.01) |
| G08B 7/06 | (2006.01) |
| G09B 5/00 | (2006.01) |
| A61B 5/00 | (2006.01) |

(52) U.S. Cl.
CPC .............. *A61B 5/165* (2013.01); *G06F 1/163* (2013.01); *G06F 3/011* (2013.01); *G06F 3/015* (2013.01); *G06F 3/016* (2013.01); *G08B 7/02* (2013.01); *G08B 7/06* (2013.01); *G09B 5/00* (2013.01); *A41D 2023/002* (2013.01); *A61B 5/6805* (2013.01); *G06F 2203/011* (2013.01)

(58) Field of Classification Search
CPC ......................... A61B 5/6804; A61B 5/6802; A41D 13/1236; A63B 2220/836; D03D 1/0088; H05K 1/038
USPC ......................................................... 434/236
See application file for complete search history.

(56) References Cited

U.S. PATENT DOCUMENTS

| | | | |
|---|---|---|---|
| 2005/0132290 | A1 | 6/2005 | Buchner |
| 2009/0197749 | A1 | 8/2009 | Merkel et al. |
| 2009/0306485 | A1 | 12/2009 | Bell |
| 2014/0070957 | A1 | 3/2014 | Longinotti-Buitoni et al. |
| 2014/0085181 | A1 | 3/2014 | Roseway et al. |
| 2014/0111414 | A1 | 4/2014 | Hayner |
| 2014/0218184 | A1 | 8/2014 | Grant et al. |
| 2015/0036856 | A1 | 2/2015 | Pruthi |

FOREIGN PATENT DOCUMENTS

| | | |
|---|---|---|
| CN | 102541257 A | 7/2012 |
| CN | 103218654 A | 7/2013 |
| CN | 103315753 A | 9/2013 |
| CN | 103970208 A | 8/2014 |
| EP | 1524586 A1 | 4/2005 |
| WO | 2011109716 A2 | 9/2011 |

OTHER PUBLICATIONS

"First Office Action and Search Report Issued in Chinese Patent Application No. 201580060471", dated Jun. 26, 2019,13 Pages. (w/o English Translation).

Appelboom, et al., "Smart Wearable Body Sensors for Patient Self-assessment and Monitoring", Archives of Public Health 2014, Aug. 22, 2014, pp. 1-9.

Berglin, "Smart Textiles and Wearable Technology—A Study of Smart Textiles in Fashion and Clothing", A report within the Baltic Fashion Project, Nov. 6, 2013, pp. 34, Swedish School of Textiles, University of Borås.

Bonanni, et al., "TapTap: A Haptic Wearable for Asynchronous Distributed Touch Therapy", Special Interest Group on Computer-Human Interaction 2006, (CHI 2006), Apr. 22-27, 2006, pp. 7, Association for Computing Machinery (ACM).

Carmichael, "A Mood Jacket to Help You Through the Day", Quantified Self—Self Knowledge Through Numbers, Jun. 13, 2010, pp. 2, Quantified Self Labs.

CDC (Centers for Disease Control and Prevention), "Autism Spectrum Disorder (ASD)", Mar. 20, 2014, pp. 5, CDC.

CVC, "Textile Sensors: Wearable Smart Garments are Driving the Quantified Self", Inside Activity Tracking, Sep. 18, 2013, pp. 5, retrieved at <<http://www.insideactivitytracking.com/textile-sensors-wearable-smart-garments-will-enable-the-quantified-self/>>.

Davis, et al., "Actuating Mood: Design of the Textile Mirror", Proceedings of the 7th International Conference on Tangible, Embedded and Embodied Interaction (TEI '13), Feb. 10-13, 2013, pp. 8, Association for Computing Machinery (ACM).

Eaton, "Does Your Phone Know How Happy You Are? The Emotion-Recognition Industry Comes Giddily of Age", Jun. 7, 2012, pp. 3, Fast Company, retrieved at <<http://www.fastcompany.com/1839275/does-your-phone-know-how-happy-you-are-emotion-recognition-industry-comes-giddily-age>>.

Grandin, "Calming Effects of Deep Touch Pressure in Patients with Autistic Disorder, College Students, and Animals", J. of Child and Adolescent Psychopharmacology, Spring 1992, pp. 7, vol. 2, No. 1, Mary Ann Liebert, Inc., Publishers, retrieved at <<http://www.grandin.com/inc/squeeze.html>>>.

Healey, et al., "Detecting Stress During Real-World Driving Tasks Using Physiological Sensors", IEEE Transactions on Intelligent Transportation Systems, Jun. 2005, pp. 28, vol. 6 Issue 2, IEEE Press.

Hernandez, et al., "Call Center Stress Recognition with Person-Specific Models", Proceedings of the 4th international conference on Affective computing and intelligent interaction (ACII 2011), Oct. 9, 2011, pp. 125-134, Part I, LNCS 6974, Springer-Verlag Berlin Heidelberg.

Hernandez, et al., "Under Pressure: Sensing Stress of Computer Users", Proceedings of the Special Interest Group on Computer Human Interaction (SIGCHI) Conference on Human Factors in Computing Systems (CHI 2014), Apr. 26-May 1, 2014, pp. 10, Association for Computing Machinery (ACM).

Hernandez, et al., "AutoEmotive: Bringing Empathy to the Driving Experience to Manage Stress", Proceedings of the 2014 companion publication on Designing Interactive Systems (DIS '14), Jun. 21-25, 2014, pp. 4, Association for Computing Machinery (ACM).

Krishna, et al., "VibroGlove: An Assistive Technology Aid for Conveying Facial Expressions", 2010 Association for Computing Machinery (ACM) Conference on Human Factors in Computing Systems (CHI 2010), Apr. 12-13, 2010, pp. 3637-3642, ACM.

Lee, et al., "Emotive Captioning", Computers in Entertainment, Aug. 2007, pp. 1-15, vol. 5, No. 2, Association for Computing Machinery (ACM).

Lee, et al., "Combining Context-Awareness with Wearable Computing for Emotion-based Contents Service", International Journal of Advanced Science and Technology, Sep. 2010, pp. 13-24, vol. 22, Science & Engineering Research Support soCiety (SERSC).

Mcewen, "Protective and Damaging Effects of Stress Mediators", The New England Journal of Medicine, Jan. 15, 1998, pp. 171-179, vol. 338, No. 3, Massachusetts Medical Society.

Mellis, et al., "Microcontrollers as Material: Crafting Circuits with Paper, Conductive Ink, Electronic Components, and an "Untoolkit"", Proceedings of the 7th International Conference on Tangible, Embedded and Embodied Interaction (TEI 2013), Feb. 10-13, 2013, pp. 8, Association for Computing Machinery (ACM).

Park, et al., "A Framework for Designing Assistive Technologies for Teaching Children With ASDs Emotions", Extended Abstracts on Human Factors in Computing Systems (CHI 2012), May 5-10, 2012, pp. 2423-2428, Association for Computing Machinery (ACM).

Perovich, et al., "Awakened Apparel: Embedded Soft Actuators for Expressive Fashion and Functional Garments", 8th International Conference on Tangible, Embedded and Embodied Interaction (TEI '14), Feb. 16-19, 2014, pp. 4, Association for Computing Machinery (ACM).

Ramirez, "QSEU14 Breakout: Emotive Wearables", Quantified Self—Self Knowledge Through Numbers, Jul. 25, 2014, pp. 2, Quantified Self Labs, retrieved at <<http://quantifiedself.com/2014/07/qseu14-breakout-emotive-wearables/>>.

Russell, "A Circumplex Model of Affect", Journal of Personality and Social Psychology, Dec. 1980, pp. 1161-1178, vol. 39, No. 6, American Psychological Association.

Sanches, et al., "Mind the Body! Designing a Mobile Stress Management Application Encouraging Personal Reflection", Pro-

(56) References Cited

OTHER PUBLICATIONS ceedings of the 8th Association for Computing Machinery (ACM) Conference on Designing Interactive Systems (DIS 2010), Aug. 16-20, 2010, pp. 47-56, ACM.

Scheirer, et al., "Affective Objects", Mit Media Laboratory Perceptual Computing Section Technical Report No. 524, May 2000, pp. 19, Massachusetts Institute of Technology (MIT) Media.

Schnepp, et al., "Combining Emotion and Facial Nonmanual Signals in Synthesized American Sign Language", Proceedings of the 14th international Association for Computing Machinery (ACM) SIGACCESS conference on Computers and accessibility (ASSETS 2012), Oct. 22-24, 2012, pp. 249-250, ACM.

Shinohara, et al., "In the Shadow of Misperception: Assistive Technology Use and Social Interactions", Proceedings of the Special Interest Group on Computer Human Interaction (SIGCHI) Conference on Human Factors in Computing Systems (CHI 2011), May 7-12, 2011, pp. 10, Association for Computing Machinery (ACM).

Stephenson, et al., "The Use of Weighted Vests with Children with Autism Spectrum Disorders and Other Disabilities", Journal of Autism and Developmental Disorders, Jul. 1, 2008, pp. 10, Springer Science+Business Media, LLC.

Sun, et al., "MouStress: Detecting Stress from Mouse Motion", Proceedings of the Special Interest Group on Computer Human Interaction (SIGCHI) Conference on Human Factors in Computing Systems (CHI 2014), Apr. 26-May 1, 2014, pp. 10, Association for Computing Machinery (ACM).

Vaucelle, et al., "Design of Haptic Interfaces for Therapy", Proceedings of the Special Interest Group on Computer Human Interaction (SIGCHI) Conference on Human Factors in Computing Systems (CHI 2009), Apr. 4-9, 2009, pp. 5, Association for Computing Machinery (ACM).

Wilkins, et al., "Humor Theories and the Physiological Benefits of Laughter", Holistic Nursing Practice, Nov./Dec. 2009, pp. 349-354, Lippincott Williams & Wilkins, Inc.

"International Preliminary Report on Patentability Issued in PCT Application No. PCT/US2015/059354", dated Jan. 18, 2017, 7 Pages.

Second Written Opinion Issued in PCT Application No. PCT/US2015/059354, dated Sep. 14, 2016, 6 Pages.

International Search Report and Written Opinion Issued in PCT Application No. PCT/US2015/059354, dated Feb. 12, 2016, 11 Pages.

Fletcher, Jerry-Daryl, U.S. Office Action, U.S. Appl. No. 14/534,581, dated Aug. 8, 2017, pp. 1-10.

Fletcher, Jerry-Daryl, U.S. Notice of Allowance, U.S. Appl. No. 14/534,581, dated Nov. 21, 2017, pp. 1-8.

"Second Office Action Issued in Chinese Patent Application No. 201580060471.4", dated Apr. 22, 2020, 26 Pages.

"Summons to Attend Oral Proceedings Issued in US Patent Application No. 15802234.3", dated Jun. 10, 2020, 7 Pages.

| Current Affective State | Actuation Cells Activated | Actuations Generated |
|---|---|---|
| Stressed | Vibration Cells | →Short Sequence Of Vibration Pulses Immediately Before Activating Other Cells |
|  | Cooling Cells | →Remove Heat From User's Body (Lower User's Body Temperature) |
|  | Audio Cells | →Play Soothing, Slow Type Of Music |
|  | Pressure Cells | →Apply Pressure To User's Body |
| Sad | Vibration Cells | →Short Sequence Of Vibration Pulses Immediately Before Activating Other Cells |
|  | Heating Cells | →Apply Heat To User's Body (Raise User's Body Temperature) |
|  | Audio Cells | →Play Cheerful, Upbeat Type Of Music |
|  | Lighting Cells | →Display Soothing Type Of Lighting Effect |
| Calm | Vibration Cells | →Short Sequence Of Vibration Pulses |
| Happy | Vibration Cells | →Short Sequence Of Vibration Pulses Immediately Before Activating Other Cells |
|  | Audio Cells | →Play Cheerful, Upbeat Type Of Music |
|  | Lighting Cells | →Display Soothing Type Of Lighting Effect |
| Excited | Vibration Cells | →Short Sequence Of Vibration Pulses Immediately Before Activating Other Cells |
|  | Cooling Cells | →Remove Heat From User's Body (Lower User's Body Temperature) |
|  | Audio Cells | →Play Cheerful, Upbeat Type Of Music |
|  | Lighting Cells | →Display Festive Type Of Lighting Effect |

FIG. 4

| Current Affective State | Actuation Cells Activated | Actuations Generated |
|---|---|---|
| Stressed | Vibration Cells | →Short Sequence Of Vibration Pulses Immediately Before Activating Other Cells |
| | Heating Cells | →Apply Heat To User's Body (Raise User's Body Temperature) |
| | Audio Cells | →Play Soothing, Slow Type Of Music |
| | Pressure Cells | →Apply Pressure To User's Body |
| Sad | Vibration Cells | →Short Sequence Of Vibration Pulses Immediately Before Activating Other Cells |
| | Heating Cells | →Apply Heat To User's Body (Raise User's Body Temperature) |
| | Audio Cells | →Play Cheerful, Upbeat Type Of Music |
| Calm | Vibration Cells | →Short Sequence Of Vibration Pulses |
| Happy | Vibration Cells | →Short Sequence Of Vibration Pulses Immediately Before Activating Other Cells |
| | Audio Cells | →Play Cheerful, Upbeat Type Of Music |
| Excited | Vibration Cells | →Short Sequence Of Vibration Pulses Immediately Before Activating Other Cells |
| | Audio Cells | →Play Cheerful, Upbeat Type Of Music |

FIG. 5

MODULAR WEARABLE DEVICE FOR CONVEYING AFFECTIVE STATE

CROSS REFERENCE TO RELATED APPLICATIONS

This application is a divisional of a prior application entitled "MODULAR WEARABLE DEVICE FOR CONVEYING AFFECTIVE STATE", which was assigned Ser. No. 14/534,581 and filed Nov. 6, 2014.

BACKGROUND

As is appreciated in the arts of psychology and cognitive science, emotion is a subjective, conscious experience that is primarily characterized by psycho-physiological expressions, biological reactions, and mental states. The physiology of emotion is closely linked to the arousal of the nervous system, with various states and strengths of arousal corresponding to particular emotions. In other words, emotion is a complex state of feeling that results in physical and psychological changes that can influence a person's behavior and the behavior of others that the person interacts with. Emotion is also linked to behavioral tendency. For example, extroverted people are more likely to outwardly express their emotions, while introverted people are more likely to conceal their emotions. Over the past two decades research on emotion has increased significantly in a number of different fields such as psychology, neuroscience, endocrinology, medicine, history, and sociology. There is a well-known correlation between a person's emotional state and their mental well-being. There is also a well-known correlation between a person's emotional state and their physical health.

SUMMARY

Wearable device implementations described herein are generally applicable to conveying information to a user. In one exemplary implementation a wearable device includes a master soft circuit cell and a plurality of actuation soft circuit cells. The master and actuation soft circuit cells are physically interconnected to form a garment that is worn by the user. The master cell and each of the actuation soft circuit cells includes an electrically non-conductive fabric covering. Each of the actuation soft circuit cells is electrically connected to and operates under the control of the master soft circuit cell. The master soft circuit cell is configured to wirelessly receive actuation instructions and activate a combination of the actuation soft circuit cells based on the received actuation instructions. Each of the actuation soft circuit cells is configured to generate a particular actuation that is perceived by one or more senses of the user whenever the actuation soft circuit cell is activated by the master soft circuit cell.

It should be noted that the foregoing Summary is provided to introduce a selection of concepts, in a simplified form, that are further described below in the Detailed Description. This Summary is not intended to identify key features or essential features of the claimed subject matter, nor is it intended to be used as an aid in determining the scope of the claimed subject matter. Its sole purpose is to present some concepts of the claimed subject matter in a simplified form as a prelude to the more detailed description that is presented below.

DESCRIPTION OF THE DRAWINGS

The specific features, aspects, and advantages of the wearable device implementations described herein will become better understood with regard to the following description, appended claims, and accompanying drawings where:

FIG. 4 is a table illustrating one implementation, in simplified form, of different combinations of actuation cells that are activated based on actuation instructions that are received by a master cell of the wearable device described herein, and the type of actuation that is generated by each of the activated actuation cells.

FIG. 5 is a table illustrating another implementation, in simplified form, of different combinations of actuation cells that are activated based on actuation instructions that are received by the master cell of the wearable device described herein, and the type of actuation that is generated by each of the activated actuation cells.

DETAILED DESCRIPTION

Figure 1:
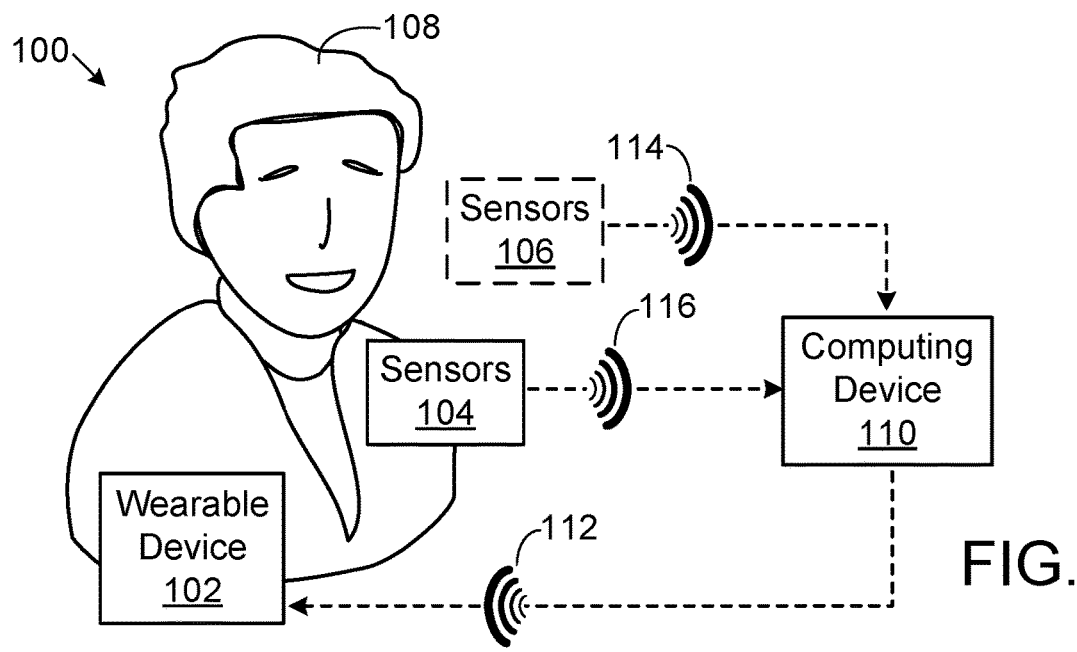
FIG. 1 is a diagram illustrating one implementation, in simplified form, of a system framework for realizing the wearable device implementations described herein.

In the following description of wearable device implementations reference is made to the accompanying drawings which form a part hereof, and in which are shown, by way of illustration, specific implementations in which the wearable device can be practiced. It is understood that other implementations can be utilized and structural changes can be made without departing from the scope of the wearable device implementations.

It is also noted that for the sake of clarity specific terminology will be resorted to in describing the wearable device implementations described herein and it is not intended for these implementations to be limited to the specific terms so chosen. Furthermore, it is to be understood that each specific term includes all its technical equivalents that operate in a broadly similar manner to achieve a similar purpose. Reference herein to "one implementation", or "another implementation", or an "exemplary implementation", or an "alternate implementation", or "one version", or "another version", or an "exemplary version", or an "alternate version" means that a particular feature, a particular structure, or particular characteristics described in connection with the implementation or version can be included in at least one implementation of the wearable device. The appearances of the phrases "in one implementation", "in another implementation", "in an exemplary implementation", "in an alternate implementation", "in one version", "in another version", "in an exemplary version", and "in an alternate version" in various places in the specification are not necessarily all referring to the same implementation or version, nor are separate or alternative implementations/versions mutually exclusive of other implementations/versions. Yet furthermore, the order of process flow representing one or more implementations or versions of the wearable device does not inherently indicate any particular order not imply any limitations of the wearable device.

As utilized herein, the terms "component," "system," "client" and the like are intended to refer to a computer-related entity, either hardware, software (e.g., in execution), firmware, or a combination thereof. For example, a component can be a process running on a processor, an object, an executable, a program, a function, a library, a subroutine, a computer, or a combination of software and hardware. By way of illustration, both an application running on a server and the server can be a component. One or more components can reside within a process and a component can be localized on one computer and/or distributed between two or more computers. The term "processor" is generally understood to refer to a hardware component, such as a processing unit of a computer system.

Furthermore, to the extent that the terms "includes," "including," "has," "contains," variants thereof, and other similar words are used in either this detailed description or the claims, these terms are intended to be inclusive, in a manner similar to the term "comprising", as an open transition word without precluding any additional or other elements.

1.0 Introduction

This section introduces several different concepts, in a simplified form, that are employed in the more detailed description of the wearable device implementations that is presented below.

As is appreciated in the art of psychology, the term "affect" generally refers to an emotion or feeling a person experiences in response to (e.g., in reaction to) one or more stimuli. Accordingly, the term "affective state" is used herein to refer to the emotional state of either a person or a group of two or more people. Due to the aforementioned well-known correlations between a person's emotional state and their physical health and mental well-being, a person's ability to identify, interpret and constructively react to their own current affective state can significantly enhance their physical health and mental well-being. Additionally, a person's ability to identify, interpret and constructively react to the current affective state of another person can significantly enhance the person's success in communicating and/or negotiating with the other person.

Due to the nature of certain disabilities, many people with one or more disabilities have difficulty identifying, interpreting and reacting to the current affective state of others. People with certain disabilities also have difficulty identifying, interpreting, expressing and constructively reacting to their own current affective state. For example, a person with a vision impairment may not be able to receive the meaningful visual cues (e.g., facial expressions and body language, among others) that are commonly associated with communicating emotions, thus making it difficult for a vision-impaired person to identify, interpret and react to the current affective state of other people. A person with a hearing impairment may not be able to receive the meaningful auditory cues (e.g., verbal cues, among others) that are commonly associated with communicating emotions, thus making it difficult for a hearing-impaired person to identify, interpret and react to the current affective state of other people. A person with a speech impairment and the elderly may have difficulty conveying their affective state to other people. A person with Autism Spectrum Disorder often has difficulty recognizing, articulating and constructively reacting to their own current affective state, and may also have difficulty interpreting and reacting to the current affective state of other people.

As is appreciated in the arts of lifelogging and self-tracking (also known as auto-analytics and self quantification), Quantified Self is an increasingly popular movement in which a person uses technology to routinely collect (e.g., measure and/or record) various types of data about himself or herself as they proceed through their daily life for goals such as self-awareness, self-reflection and self-improvement. This collected data can then be routinely analyzed using conventional methods and the results of this data analysis can be provided to the person in the form of quantitative information about their everyday activities. In other words, Quantified Self is self-knowledge through self-tracking with technology. The various types of data about the person that are collected and analyzed by the Quantified Self movement are herein sometimes collectively referred to as quantified self data. Quantified self data can be categorized into two classes, namely data about the person's physiology and data about the person's activities (e.g., physical activities, sleep, food intake, and alcohol intake, among many others).

Many different types of data about the person's physiology can be collected by the Quantified Self movement, examples of which include an electrocardiography (ECG) signal for the person, one or more electroencephalography (EEG) signals for the person, a skin temperature measurement for the person, a skin conductance response (also known as electrodermal response, electrodermal activity and galvanic skin response) measurement for the person, a heart rate and/or heart rate variability measurement for the person, a blood oxygen-level measurement for the person, and a blood pressure measurement for the person, among others. Many different types of data about the person's activities can also be collected by the Quantified Self movement, examples of which include an ElectroVisuoGram (EVG) signal for the person, video and/or images of the person's face and/or body, video and/or images of the person's environment, a geolocation measurement for the person, an altitude measurement for the person, a linear velocity measurement for the person, an acceleration measurement for the person, a physical orientation measurement for the person, sound from the person's environment (which will include speech from the person and any others who may be in the person's environment), the light-level in the person's environment, the moisture-level in the person's environment (which can indicate when the person is immersed in water), the number of steps taken by the person, the number of stairs climbed by the person, the distance traveled by the person, the person's sleep schedule and/or sleep quality, the amount of alcohol consumed by the person, and the types and quantities of food consumed by the person, among others.

Quantified self data about the person can be collected from many different modalities. For example, quantified self data about the person can be collected from one or more sensors that are physically attached to (e.g., worn on, among other attachment methods) the person's body. Examples of such sensors include a plurality of ECG electrodes, a plurality of EEG electrodes, one or more video cameras, a microphone, a global positioning system receiver, a skin temperature sensor, a galvactivator, an accelerometer, a gyroscope, an altimeter, a moisture sensor, a heart rate sensor, a pedometer, a pulse oximeter, or a blood pressure monitor, among others. Quantified self data about the person can also be collected from one or more devices that the person has occasion to come in physical contact with throughout the course of their day (such as a pressure-sensitive keyboard or a capacitive mouse, among others). Quantified self data about the person can also be collected from one or more sensors that are remote from but in the immediate vicinity of the person (such as a surveillance camera or a microphone, among others). Quantified self data about the person can also be collected from information that is manually entered into one or more computing devices (such as a smartphone, tablet computer, wearable computer, laptop computer, or other type of personal computer).

2.0 Modular Wearable Device for Conveying Affective State

The term "user" is used herein to refer to a person who is wearing the wearable device implementations described herein. The wearable device implementations are generally applicable to conveying (e.g., communicating) information to a user. It is noted that the wearable device implementations can convey many different types of information to the user. In an exemplary implementation of the wearable device that is described in more detail hereafter, the wearable device conveys the current affective state of the user to the user. As will be appreciated from the more detailed description that follows, this exemplary implementation alerts the user to (e.g., makes the user aware of) their current affective state, thus allowing the user to reflect on (e.g., identify and interpret) and react to their current affective state, and informs the user when and how their affective state changes. This exemplary implementation can also change the user's current affective state for the better in circumstances where such a change will enhance their physical health and mental well-being (e.g., stress reduction).

As will also be appreciated from the more detailed description that follows, the wearable device implementations described herein are advantageous for various reasons such as the following. The wearable device implementations provide a user with a cost effective, reliable and easy to use way to enhance their physical health and mental well-being, and enhance their success in communicating and/or negotiating with other people. The wearable device implementations also employ a universal design that that is suitable for everyday use by users with various disabilities (such as a vision impairment, or a hearing impairment, or a speech impairment, or Autism Spectrum Disorder, among other disabilities) and users with no disabilities at all. In other words, the wearable device implementations are inherently accessible for many types of users ranging in age from infancy to old age, including users both with and without disabilities. While the wearable device implementations are beneficial to everyone, they can be especially beneficial to users with disabilities and the elderly. The wearable device implementations are also lightweight, supple, breathable and comfortable, and can be discreetly worn for long periods of time without detracting from a user's ability to perform their normal daily activities. The wearable device implementations also compliment users' current strategies for coping with and managing their emotions.

The wearable device implementations described herein also employ a modular, soft-circuit-based design that allows the wearable device implementations to be realized in a wide variety of garment form factors that look fashionable, blend in with the latest fashion trends, and can be discreetly worn every day. The wearable device implementations thus reduce the stigma of wearable and assistive technologies, which is especially advantageous for users with disabilities. This modular design also allows the wearable device implementations to accommodate each user's sensory capabilities (e.g., limitations) and preferences. In other words, the wearable device implementations can be individually customized to meet the specific personal needs and preferences of many types of users, including those with various disabilities. The wearable device implementations also provide each user with an on-body experience that can continuously convey affective state and other types of information to the user in a natural, subtle, and in-the-moment way. The wearable device implementations also interact with the user's senses in a manner that can mitigate a negative affective state (e.g., stressed or sad, among others) and enhance a positive affective state (e.g., calm or happy, among others). The wearable device implementations also allow each user to reflect on and react to both positive and negative patterns in their behavior.

2.1 System Framework

This section describes two exemplary implementations of a system framework that can be used to realize the wearable device implementations described herein. It is noted that in addition to the system framework implementations described in this section, various other system framework implementations may also be used to realize the wearable device implementations.

FIG. 1 illustrates one implementation, in simplified form, of a system framework for realizing the wearable device implementations described herein. As exemplified in FIG. 1, the system framework 100 includes one or more sensors 104 that are physically attached to the body of a user 108 and either continuously or routinely generate quantified self data about the user. Examples of such sensors 104 have been provided heretofore. The system framework 100 can optionally also include one or more sensors 106 that are remote from but in the immediate vicinity of the user 108 and either continuously or routinely generate additional quantified self data about the user. Examples of such sensors 106 have also been provided heretofore. The system framework 100 can optionally also include one or more devices (not shown) that the user 108 has occasion to come in physical contact with throughout the course of their day and generate additional quantified self data about the user whenever the user makes physical contact with them. Examples of such devices have also been provided heretofore.

Referring again to FIG. 1, the system framework 100 also includes a local computing device 110 that is located in the vicinity of the user 108. Examples of such a local computing device 110 include a smartphone, a laptop computer, a desktop computer, and a sever computer. The system framework 100 also includes a wearable device 102 that is being worn by the user 108 and conveys information to the user. The local computing device 110 is configured to wirelessly receive 114 and 116 the quantified self data about the user 108 that is being generated by the sensors 104 and 106, and may also be generated by the just-described devices that the user has occasion to come in physical contact with. The local computing device 110 is further configured to determine the current affective state of the user 108 from the received quantified self data. Examples of the different affective states that can be determined from the received quantified self data are described in more detail hereafter.

Referring again to FIG. 1, in one version of the system framework 100 implementation the local computing device 110 is further configured to generate actuation instructions that specify a prescribed set of actuations which distinctly conveys the current affective state of the user 108 to the user, and wirelessly transmit 112 these actuation instructions to the wearable device 102. The term "actuation" is used herein to refer to a user feedback signal that is perceived by (e.g., interacts with) one or more of the user's 108 senses. As will be described in more detail hereafter, the wearable device 102 is accordingly configured to wirelessly receive 112 the actuation instructions transmitted from the local computing device 110 and generate the prescribed set of actuations that is specified by the actuation instructions. Exemplary sets of actuations which distinctly convey each of the different affective states that can be determined are also described in more detail hereafter. As will be appreciated from the more detailed description that follows, the set of actuations that is generated by the wearable device can advantageously mitigate a negative affective state and enhance a positive affective state.

Referring again to FIG. 1, in another version of the system framework 100 implementation, rather than the local computing device 110 wirelessly transmitting 112 actuation instructions to the wearable device 102 as just described, the local computing device 110 is configured to wirelessly transmit 112 information specifying the current affective state of the user 108 to the wearable device 102. The wearable device 102 is accordingly configured to wirelessly receive 112 the information transmitted from the local computing device 110 and generate a prescribed set of actuations which distinctly conveys the current affective state of the user 108 to the user. The wireless communication (e.g., 114 and 116) of the quantified self data about the user 108, and the wireless communication 112 of both the actuation instructions and the information specifying the current affective state of the user, can be realized using various wireless networking technologies. For example, in one version of the wearable device implementations this wireless communication 112/114/116 is realized using a conventional Bluetooth personal area network. In another version of the wearable device implementations the wireless communication 112/114/116 is realized using a conventional Wi-Fi local area network. In yet another version of the wearable device implementations the wireless communication 112/114/116 is realized using a combination of different wireless networking technologies.

Figure 2:
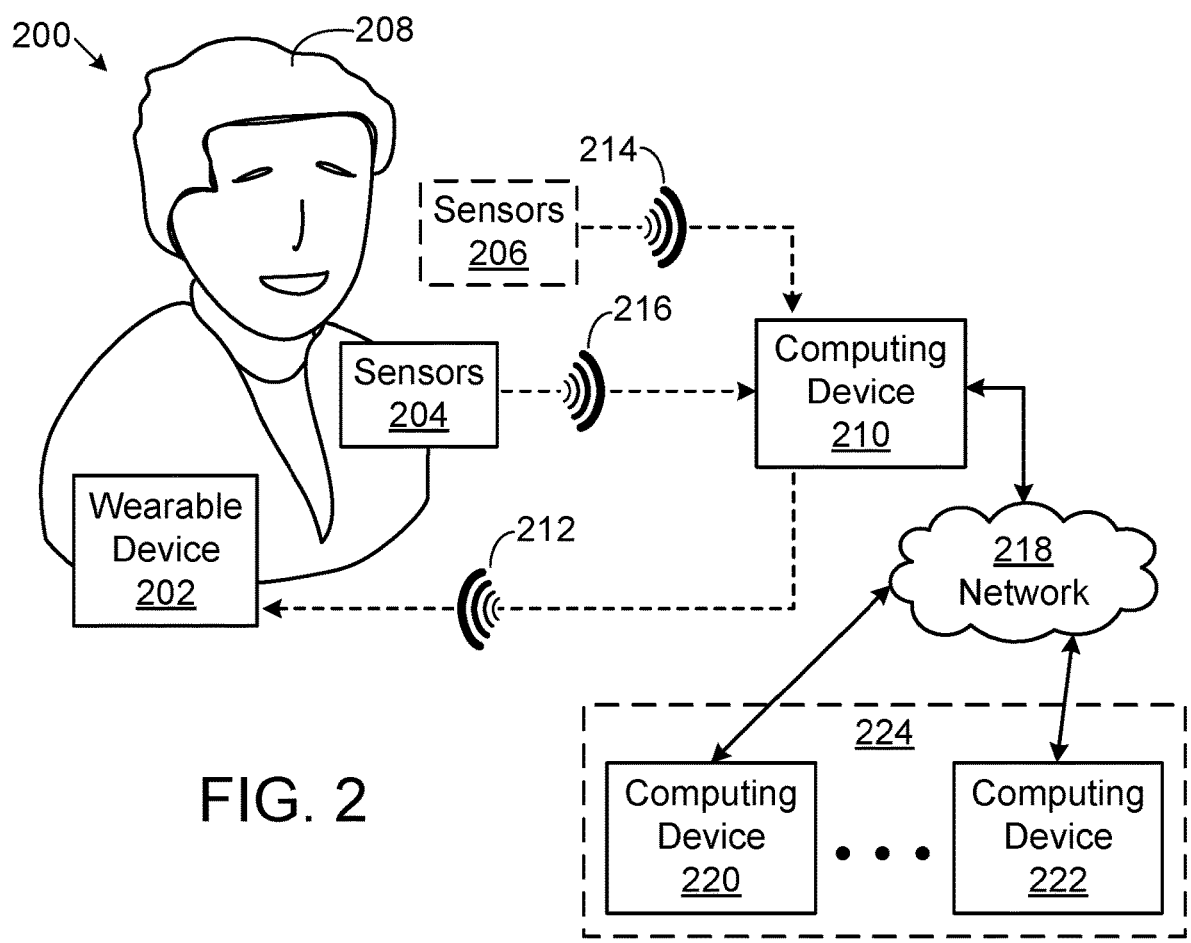
FIG. 2 is a diagram illustrating another implementation, in simplified form, of a system framework for realizing the wearable device implementations described herein.

FIG. 2 illustrates another implementation, in simplified form, of a system framework for realizing the wearable device implementations described herein. As exemplified in FIG. 2, the system framework 200 includes one or more sensors 204 that are physically attached to the body of a user 208 and either continuously or routinely generate quantified self data about the user. The system framework 200 can optionally also include one or more sensors 206 that are remote from but in the immediate vicinity of the user 208 and either continuously or routinely generate additional quantified self data about the user. The system framework 200 can optionally also include one or more devices (not shown) that the user 208 has occasion to come in physical contact with throughout the course of their day and generate additional quantified self data about the user whenever the user makes physical contact with them.

Referring again to FIG. 2, the system framework 200 also includes a local computing device 210 that is located in the vicinity of the user 208. Examples of such a local computing device 210 include a smartphone, a laptop computer, a desktop computer, and a sever computer. The system framework 200 also includes a wearable device 202 that is being worn by the user 208 and conveys information to the user. The local computing device 210 is configured to wirelessly receive 214 and 216 the quantified self data about the user 208 that is being generated by the sensors 204 and 206, and may also be generated by the devices that the user has occasion to come in physical contact with. The local computing device 210 is further configured to forward the received quantified self data over a data communication network 218 such as the Internet (among other types of networks) to a cloud service 224 that operates on one or more other computing devices 220 and 222 that are remotely located from the local computing device 210. The remote computing devices 220 and 222 can also communicate with each other via the network 218. The term "cloud service" is used herein to refer to a web application that operates in the cloud and can be hosted on (e.g., deployed at) a plurality of data centers that can be located in different geographic regions (e.g., different regions of the world).

Referring again to FIG. 2 and as will be described in more detail hereafter, in one version of the system framework 200 implementation the cloud service 224 receives the quantified self data forwarded from the local computing device 210, determines the current affective state of the user 208 from the received quantified self data, generates actuation instructions that specify a prescribed set of actuations which distinctly conveys the current affective state of the user 208 to the user, and transmits these actuation instructions to the local computing device. The local computing device 210 is accordingly further configured to receive the actuation instructions transmitted from the cloud service 224 and wirelessly forward 212 them to the wearable device 202. The wearable device 202 is accordingly configured to wirelessly receive 212 the actuation instructions forwarded from the local computing device 210 and generate the prescribed set of actuations that is specified by the actuation instructions. It is noted that although the system framework 200 depicts a single local computing device 210 that is wirelessly communicating 212 with a single wearable device 202, yet another system framework implementation (not shown) is also possible where the cloud service is provided to a plurality of local computing devices, where each of the local computing devices wirelessly communicates with a different set of sensors and a different wearable device that is being worn by a different user.

Referring again to FIG. 2, in another version of the system framework 200 implementation, rather than the cloud service 224 transmitting actuation instructions to the local computing device 210 which receives these instructions and wirelessly forwards 212 them to the wearable device 202 as just described, the cloud service transmits information specifying the current affective state of the user 208 to the local computing device. The local computing device 210 is accordingly configured to receive this information from the cloud service 224 and wirelessly forward 212 it to the wearable device 202. The wearable device 202 is accordingly configured to wirelessly receive 212 the information forwarded from the local computing device 210 and generate a prescribed set of actuations which distinctly conveys the current affective state of the user 208 to the user. The wireless communication (e.g., 214 and 216) of the quantified self data about the user 208, and the wireless communication 212 of both the actuation instructions and the information specifying the current affective state of the user, can be realized in any of the ways described previously in this section.

2.2 Wearable Device Hardware Architecture

Figure 3:
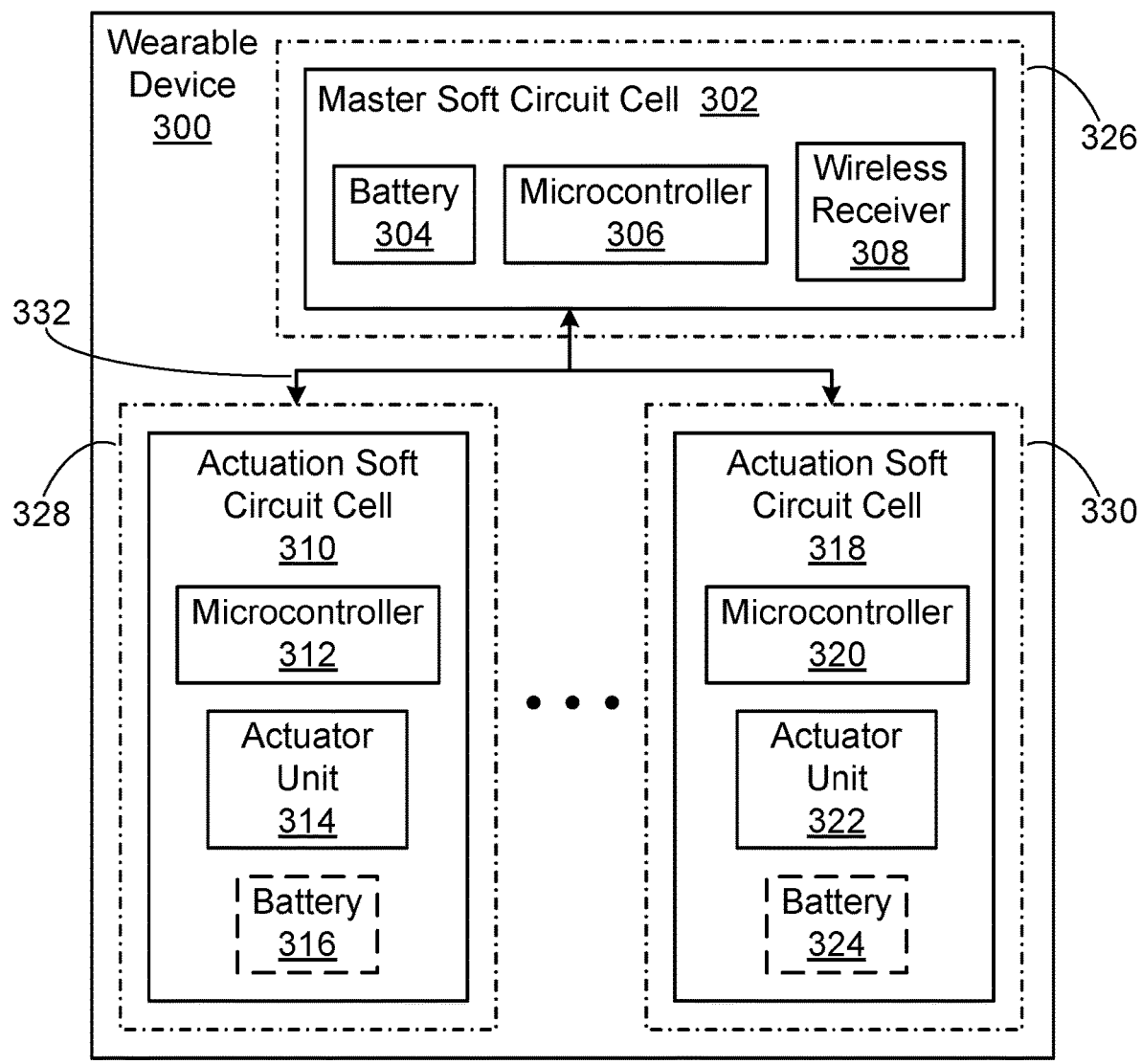
FIG. 3 is a diagram illustrating an exemplary implementation, in simplified form, of a hardware architecture for the wearable device described herein.

FIG. 3 illustrates an exemplary implementation, in simplified form, of a hardware architecture for the aforementioned wearable device that conveys information to a user. As exemplified in FIG. 3, the wearable device 300 includes a master soft circuit cell (hereafter simply referred to as a master cell) 302 and a plurality of actuation soft circuit cells (hereafter simply referred to as actuation cells) 310 and 318. Generally speaking and as is appreciated in the art of electronic textiles (also known as e-textiles, smart textiles and smart fabrics), the term "soft circuit" refers to an electronic circuit having a plurality of discrete electronic components that are electrically interconnected by one or more flexible, electrically conductive materials, where both the electronic components and the electrically conductive materials are adhered to a flexible, electrically non-conductive base material. Accordingly, the master and actuation cells 302/310/318 are pliable electronic circuits. As will be described in more detail hereafter, the master cell 302 and actuation cells 310 and 318 are physically interconnected to form a garment (not shown) that is worn by the user (not shown) on a desired portion of their body. The pliability of these cells 302/310/318 allows the garment to conform to the shape of the portion of the user's body upon which the garment is being worn.

Referring again to FIG. 3, the master cell 302 includes an electrically non-conductive fabric covering 326. Each of the actuation cells 310 and 318 also includes an electrically non-conductive fabric covering 328 and 330. Each of the actuation cells 310 and 318 is electrically connected 332 to and operates under the control of the master cell 302. This electrical connection 332 allows the master cell 302 to supply power to and communicate with (e.g., activate and deactivate, among other types of communication) each of the actuation cells 310 and 318. The master cell 302 is configured to wirelessly receive the aforementioned actuation instructions that specify a prescribed set of actuations, and activate a combination of the actuation cells 310 and 318 based on the received actuation instructions. Each of the actuation cells 310 and 318 is configured to generate a particular actuation that is perceived by one or more senses of the user whenever the actuation cell is activated by the master cell 302. The just-described modularity of the wearable device 300 is advantageous in that it allows the configuration of the device to be customized to include the types and quantities of actuation cells 310 and 318 that meet the personal needs and preferences of the user.

Referring again to FIG. 3, the master cell 302 includes a master battery 304, a master microcontroller 306, and a wireless receiver 308. Various types of batteries, microcontrollers and wireless receivers can be used in the master cell 302. For example, in an exemplary implementation of the wearable device 300 a conventional 3.7 volt, 800 milliampere-hour, lithium-ion battery pack is used for the master battery 304, a conventional Arduino Beetle microcontroller is used for the master microcontroller 306, and either a conventional Bluetooth personal area network receiver module or a conventional Wi-Fi local area network receiver module is used for the wireless receiver 308. The master battery 304 supplies power to the master microcontroller 306 and the wireless receiver 308, and also supplies power over a power distribution bus portion (not shown) of the electrical connection 332 to each of the actuation cells 310 and 318. The wireless receiver 308 receives the actuation instructions and passes them to the master microcontroller 306. The master microcontroller 306 interprets the received actuation instructions and sends commands over a communication bus portion (not shown) of the electrical connection 332 to each of the actuation cells 310 and 318, where these commands cause the actuation soft circuit cells whose particular actuation is in the set of actuations specified by the received actuation instructions to be activated, and cause the actuation soft circuit cells whose particular actuation is not in this set to be deactivated.

Referring again to FIG. 3, each of the actuation cells 310 and 318 includes a slave microcontroller 312 and 320 and an actuator unit 314 and 322. Certain of the actuation cells 310 and 318 may also include a secondary battery 316 and 324 that is used to supply power to certain types of actuator units 314 and 322 that need more power than can be provided by the master battery 304 (such as the heating and cooling elements that are described in more detail hereafter). Various types of microcontrollers, actuator units and batteries can be used in the actuation cells 310 and 318. For example, in an exemplary implementation of the wearable device 300 the Arduino Beetle microcontroller is used for the slave microcontroller 312 and 320 and the 3.7 volt, 800 milliampere-hour, lithium-ion battery pack is used for the secondary battery 316 and 324 when necessary. Exemplary types of actuator units that are used are described in more detail hereafter. Each of the actuation cells 310 and 318 receives power from the master cell 302 over the power distribution bus portion of the electrical connection 332 and provides this received power to its slave microcontroller 312 and 320 and actuator unit 314 and 322. The slave microcontroller 312 and 320 on each of the actuation cells 310 and 318 also receives the just-described commands from the master cell 302 over the communication bus portion of the electrical connection 332. Whenever a given slave microcontroller (e.g., 312) on a given actuation cell (e.g., 310) receives an activation command from the master cell 302, the slave microcontroller turns on the cell's actuator unit (e.g., 314). Whenever a given slave microcontroller (e.g., 320) on a given actuation cell (e.g., 318) receives a deactivation command from the master cell 302, the slave microcontroller turns off the cell's actuator unit (e.g., 322).

Referring again to FIG. 3, in an exemplary implementation of the wearable device 300 the electrical connection 332 between the master cell 302 and each of the actuation cells 310 and 318 is realized using a 4-wire bus (not shown) that serially passes through the master and actuation cells, and is driven and controlled by the master cell. Two of the wires in the 4-wire bus function as a power distribution bus, and the other two of the wires in the 4-wire bus function as a serial communication bus. In other words, in this implementation the electrical connection 332 includes a 2-wire power distribution bus (not shown) and a 2-wire serial communication bus (not shown). The power distribution bus supplies power from the master battery 304 to each of the actuation cells 310 and 318. The serial communication bus allows the master microcontroller 306 to communicate with each of the slave microcontrollers 312 and 320. More particularly and by way of example but not limitation, the serial communication bus distributes the aforementioned commands that are sent by the master microcontroller 306 to each of the each of the slave microcontrollers 312 and 320. In an exemplary version of this implementation the conventional Inter-Integrated Circuit (I2C) bus and related message protocol is used for the serial communication bus. Accordingly, in this exemplary version the commands follow the I2C message protocol.

2.3 Wearable Device Actuations

The wearable device implementations described herein can determine various current affective states of the user from the aforementioned quantified self data about the user that is received. In an exemplary implementation of the wearable device the current affective state of the user that is determined from the received quantified self data is either stressed, sad, calm, happy or excited. It will be appreciated that these five different affective states are derived from the conventional circumplex model of affect as defined by James A. Russell in 1980, and represent a balance of positive and negative affective states that are familiar to everyone. It is noted that alternate implementations of the wearable device are possible where either less than five or more than five different affective states, or other combinations of affective states, can be determined from the received quantified self data.

Referring again to FIG. 3, the wearable device 300 can include many different types and combinations of actuation cells 310 and 318, where the particular types of actuation cells and the particular quantity of each type that is employed in the wearable device can be customized to meet the personal needs and preferences of the user. By way of example but not limitation, a given actuation cell in the wearable device can be either a heating cell, or a cooling cell, or an audio cell, or a vibration cell, or a lighting cell, or a pressure cell, or a rubbing cell. Each of these different types of actuation cells and the type of actuation it generates when it is activated by the master cell 302 are described in more detail hereafter. As will be appreciated from the more detailed description that follows, these seven exemplary types of actuation cells are advantageous in that they, individually and in various combinations, generate actuations that are accessible for the aforementioned many types of users. These types of actuation cells are also advantageous in that they provide a rich, multi-modal language for conveying affective state information to the user.

In an exemplary implementation of the wearable device described herein the heating cell uses a heating element for its actuator unit. In an exemplary version of this implementation the heating cell also includes the aforementioned secondary battery. When the heating element on the heating cell is turned on by the cell's slave microcontroller the secondary battery supplies power to the heating element, which subsequently generates heat that is applied to the portion of the user's body where the heating cell is located. The heating cell is thus configured to generate a heating actuation that warms the user (e.g., raises their body temperature) whenever the heating cell is activated by the master cell. In an exemplary version of this implementation the heating element is a conventional 40-gauge resistive wire having a prescribed length. It is noted that various other types of heating elements can also be used.

In an exemplary implementation of the wearable device described herein the cooling cell uses a cooling element for its actuator unit. In an exemplary version of this implementation the cooling cell also includes the secondary battery. When the cooling element on the cooling cell is turned on by the cell's slave microcontroller the secondary battery supplies power to the cooling element, which subsequently removes heat from the portion of the user's body where the cooling cell is located. The cooling cell is thus configured to generate a cooling actuation that cools the user (e.g., lowers their body temperature) whenever the cooling cell is activated by the master cell. In an exemplary version of this implementation the cooling element is a conventional thermoelectric cooling device (such as a Peltier cooling device, or the like). It is noted that various other types of cooling elements can also be used.

In an exemplary implementation of the wearable device described herein the audio cell uses an audio output element for its actuator unit. When the audio output element on the audio cell is turned on by the cell's slave microcontroller the audio output element plays a desired one of a plurality of different of sounds (which can include various types of music, environmental sounds, tones, verbal information, or the like) that may be heard by the user and may also be felt on the portion of the user's body where the audio cell is located. The audio cell is thus configured to generate an audio actuation that may be heard and felt by the user whenever the audio cell is activated by the master cell. In an exemplary version of this implementation the audio output element is a conventional Adafruit "Music Maker" MP3 Shield that is electronically coupled to either a conventional miniature loudspeaker or conventional headphones that are worn by the user. It is noted that various other types of audio output elements can also be used.

In an exemplary implementation of the wearable device described herein the vibration cell uses a vibration element for its actuator unit. When the vibration element on the vibration cell is turned on by the cell's slave microcontroller the vibration element vibrates, where this vibration may be felt on the portion of the user's body were the vibration cell is located. The vibration cell is thus configured to generate a vibration actuation that may be felt by the user whenever the vibration cell is activated by the master cell. It will be appreciated that the vibration actuation may be either a continuous vibration (e.g., the vibration element may be turned on and then left on) or a prescribed pattern of vibration pulses which may have varying durations (e.g., the vibration element may be turned on and off repeatedly in a prescribed manner). In an exemplary version of this implementation the vibration element is one or more conventional vibration motors. It is noted that other types of vibration elements can also be used.

In an exemplary implementation of the wearable device described herein the lighting cell uses a light output element for its actuator unit. When the light output element on the lighting cell is turned on by the cell's slave microcontroller the light output element displays a desired one of a plurality of different types of lighting effects (examples of which are described in more detail hereafter) that may be seen by the user. The lighting cell is thus configured to generate a lighting actuation that may be seen by the user whenever the lighting cell is activated by the master cell. In an exemplary version of this implementation the light output element is either a conventional ribbon LED (light emitting diode) strip or a conventional LED matrix (such as the Adafruit NeoPixel Matrix, or the like). It is noted that these particular types of light output elements are advantageous in that they can produce coarse, low-resolution color and brightness changes which can be visually perceived by some visually impaired users. However, various other types of light output elements can also be used. In the case where the user has privacy concerns, the lighting effects that are displayed by the lighting cell can employ subtle color changes that are considered to be aesthetically pleasing and fashionable by others, who need not be aware that the lighting effects encode information for the user.

In an exemplary implementation of the wearable device described herein the pressure cell uses a pressure producing element for its actuator unit. When the pressure producing element on the pressure cell is turned on by the cell's slave microcontroller the pressure producing element applies pressure to the portion of the user's body where the pressure cell is located. The pressure cell is thus configured to generate a pressure actuation that may be felt by the user whenever the pressure cell is activated by the master cell. It will be appreciated that this pressure actuation generally serves to reduce the user's stress level, especially for users with autism since they frequently use pressure to help them focus and relieve the stress of sensory overload. In an exemplary version of this implementation the pressure producing element is a conventional micropump (such as a piezoelectric micropump, or the like) that is air-flow-coupled to an inflatable bladder, where the bladder is either inflated (thus increasing the amount of pressure applied to the user's body) or deflated (thus decreasing the amount of pressure applied to the user's body) when the pressure cell is activated by the master cell.

In an exemplary implementation of the wearable device described herein the rubbing cell uses a shape changing element for its actuator unit. When the shape changing element on the rubbing cell is turned on by the cell's slave microcontroller the shape changing element changes the physical shape of the cell (e.g., deforms the cell), thus causing the cell to rub against the portion of the user's body where the rubbing cell is located. The rubbing cell is thus configured to generate a rubbing actuation that may be felt by the user whenever the rubbing cell is activated by the master cell. In an exemplary version of this implementation the shape changing element is a conventional nickel titanium shape memory wire (also known as nitinol wire and FLEXI-NOL® (a registered trademark of Dynalloy, Inc.) wire) having a prescribed length. It is noted that various other types of shape changing elements can also be used.

FIG. 4 illustrates one implementation, in simplified form, of different combinations of actuation cells that are activated based on the actuation instructions that are received by the master cell in the wearable device, and the type of actuation that is generated by each of the activated actuation cells in the wearable device. As exemplified in FIG. 4, whenever the current the current affective state of the user that is determined from the received quantified self data changes to stressed from another affective state, the actuation instructions will specify that each of the vibration cells in the wearable device is to generate a prescribed short sequence of (e.g., two successive) vibration pulses each having a prescribed duration (e.g., 250 milliseconds) immediately before activating the cooling, audio and pressure cells, where these vibration pulses serve to alert the user to a change in their affective state. The actuation instructions will further specify that each of the cooling cells in the wearable device is to be activated, which serves to remove heat from the user's body (thus lowering their body temperature) and may help reduce the user's stress level. The actuation instructions will further specify that each of the audio cells in the wearable device is to be activated and play a soothing, slow type of music, which can also help reduce the user's stress level. The actuation instructions will further specify that each of the pressure cells in the wearable device is to be activated, which serves to apply pressure to the user's body and can also help reduce the user's stress level. The actuation instructions will further specify that any other types of actuation cells that are in the wearable device are to be deactivated.

Referring again to FIG. 4, whenever the current affective state of the user that is determined from the received quantified self data changes to sad from another affective state, the actuation instructions will specify that each of the vibration cells in the wearable device is to generate the just-described short sequence of vibration pulses immediately before activating the heating, audio and lighting cells, where these vibration pulses serve to alert the user to a change in their affective state. The actuation instructions will further specify that each of the heating cells in the wearable device is to be activated, which serves to apply heat to the user's body (thus raising their body temperature) and can help transition the user out of their sad state. The actuation instructions will further specify that each of the audio cells in the wearable device is to activated and play a cheerful, upbeat type of music, which can also help transition the user out of their sad state. The actuation instructions will further specify that each of the lighting cells in the wearable device is to be activated and display a soothing type of lighting effect, which can also help transition the user out of their sad state. The actuation instructions will further specify that any other types of actuation cells that are in the wearable device are to be deactivated.

Referring again to FIG. 4, whenever the current affective state of the user that is determined from the received quantified self data changes to calm from another affective state, the actuation instructions will specify that each of the vibration cells in the wearable device is to generate the aforementioned short sequence of vibration pulses which serve to alert the user to a change in their affective state. The actuation instructions will further specify that any other types of actuation cells that are in the wearable device are to be deactivated. In other words, after the sequence of vibration pulses has been generated, the device will remain dormant until the current affective state of the user changes.

Referring again to FIG. 4, whenever the current affective state of the user that is determined from the received quantified self data changes to happy from another affective state, the actuation instructions will specify that each of the vibration cells in the wearable device is to generate the aforementioned short sequence of vibration pulses immediately before activating the audio and lighting cells, where these vibration pulses serve to alert the user to a change in their affective state. The actuation instructions will further specify that each of the audio cells in the wearable device is to be activated and play a cheerful, upbeat type of music, which can help reinforce the user's happy state. The actuation instructions will further specify that each of the lighting cells in the wearable device is to be activated and display a soothing type of lighting effect, which can also help reinforce the user's happy state. The actuation instructions will further specify that any other types of actuation cells that are in the wearable device are to be deactivated.

Referring again to FIG. 4, whenever the current affective state of the user that is determined from the received quantified self data changes to excited from another affective state, the actuation instructions will specify that each of the vibration cells in the wearable device is to generate the aforementioned short sequence of vibration pulses immediately before activating the cooling, audio and lighting cells, where these vibration pulses serve to alert the user to a change in their affective state. The actuation instructions will further specify that each of the cooling cells in the wearable device is to be activated, which serves to remove heat from the user's body (thus lowering their body temperature). The actuation instructions will further specify that each of the audio cells in the wearable device is to be activated and play a cheerful, upbeat type of music. The actuation instructions will further specify that each of the lighting cells in the wearable device is to be activated and display a festive type of lighting effect. The actuation instructions will further specify that any other types of actuation cells that are in the wearable device are to be deactivated.

FIG. 5 illustrates another implementation, in simplified form, of different combinations of actuation cells that are activated based on the actuation instructions that are received by the master cell in the wearable device, and the type of actuation that is generated by each of the activated actuation cells in the wearable device. The different actuation cell combinations shown in FIG. 5 reflect the following observations. Some users favor the heating actuation of the heating cell over the cooling actuation of the cooling cell. Some users don't want their affective state visible to others, thus making the lighting actuation of the lighting cell undesirable. Some users find the heating actuation to be soothing (like a "warm hug") and effective at reducing their stress level when they are stressed. In an alternate version of this implementation, the amount of heat that is applied to the user's body when they are stressed or sad may be adjusted according to their level of stress/sadness (e.g., a higher amount of heat could convey a greater level of stress/sadness).

In addition to the different combinations of actuation cells shown in FIGS. 4 and 5, it is noted that various other combinations of actuation cells can be activated when the different affective states of the user are determined. By way of example but not limitation, depending on a given user's needs and preferences, the combinations of actuation cells that are activated for the different affective states of the user can be optimized for just conveying the user's current affective state, or can be optimized for helping the user transition out of unhealthy affective states (e.g., being stressed or sad) into healthy affective states (e.g., being calm or happy). The vibration cell can also be instructed to generate long and variable patterns of vibration pulses that can serve to massage and thus relax/calm the user when they are stressed. The rubbing cell can also be used to relax/calm the user when they are stressed. The rubbing cell can also be used to alert the user to a change in their affective state, either in place of or in addition to using the vibration cell for this purpose. Using the rubbing cell rather than the vibration cell to alert the user to a change in their affective state can be advantageous if the user has autism, since the vibration pulses may be too much stimulation for them.

2.4 Wearable Device Soft Circuits

This section provides a more detailed description of exemplary implementations of soft circuits for the aforementioned vibration cell and heating cell, and an exemplary method for electrically connecting each of the actuation cells described herein to the master cell.

Figure 6:
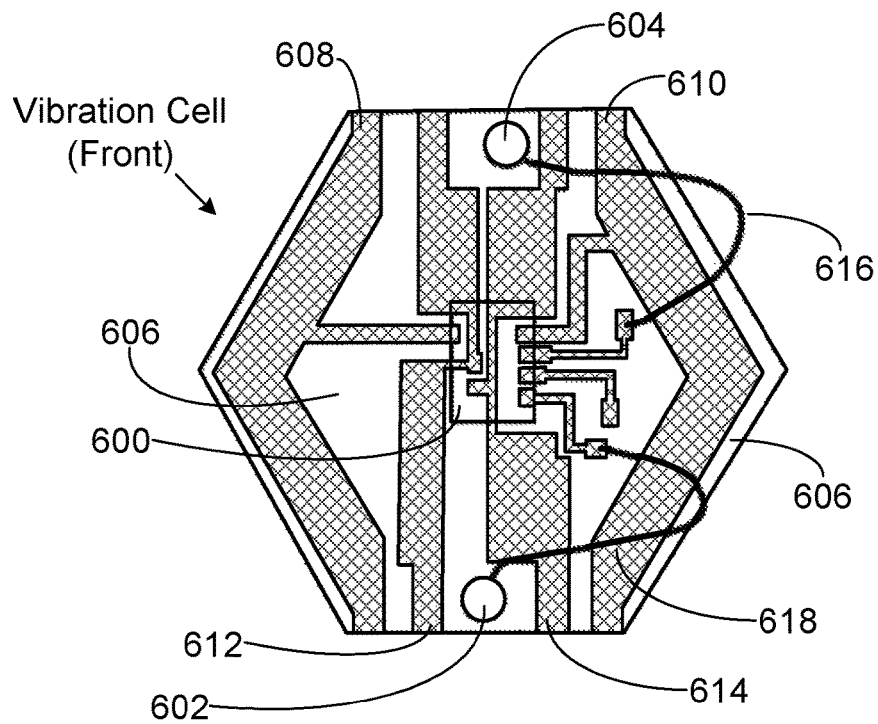
FIG. 6 is a diagram illustrating a front-side plan view of an exemplary implementation, in simplified form, of a soft circuit for a vibration cell that can be employed in the wearable device described herein.

FIG. 6 illustrates a front-side plan view of an exemplary implementation, in simplified form, of a soft circuit for the vibration cell. As exemplified in FIG. 6, the soft circuit for the vibration cell includes a slave microcontroller 600, a vibration element composed of two vibration motors 602 and 604, and a flexible, electrically non-conductive base material 606 onto which a plurality of flexible, electrically conductive circuit traces (e.g., 608/610/612/614) is adhered. Two of these circuit traces 608 and 610 form a segment of the aforementioned power distribution bus, and another two of these circuit traces 612 and 614 form a segment of the aforementioned serial communication bus. In an exemplary version of this implementation conventional copper ripstop fabric is used for each of the circuit traces 608/610/612/614, and either conventional felt or conventional cotton canvas is used for the base material 606. It will be appreciated that the vibration cell can be fabricated using various methods. In an exemplary version of this implementation the vibration cell is fabricated as follows. The circuit traces 608/610/612/614 are first adhered in a prescribed pattern to the front of a large section of the base material 606, and the vibration cell is then raster cut out of this large section. Then, the microcontroller 600 and wires (e.g., 616 and 618) emanating from each of the vibration motors 602 and 604 are electrically secured (using a conventional, electrically conductive adhesive transfer tape such as that manufactured by 3M, or the like) to appropriate locations on the circuit traces, and the vibration motors are secured to appropriate locations on the front of the base material 606.

Figure 7:
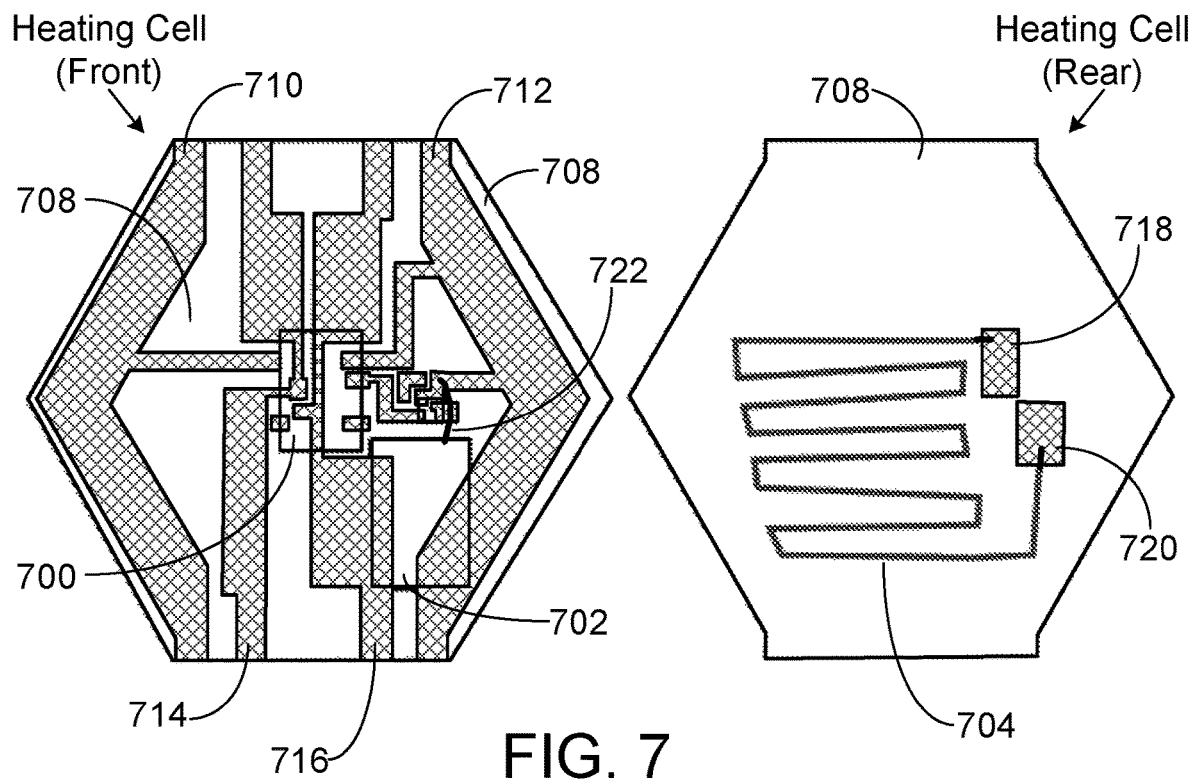
FIG. 7 is a diagram illustrating a front-side and rear-side plan view of an exemplary implementation, in simplified form, of a soft circuit for a heating cell that can be employed in the wearable device described herein.

FIG. 7 illustrates a front-side and rear-side plan view of an exemplary implementation, in simplified form, of a soft circuit for the heating cell. As exemplified in FIG. 7, the soft circuit for the heating cell includes a slave microcontroller 700, a secondary battery 702, a heating element composed of a resistive wire 704, and a flexible electrically non-conductive base material 708 onto which a plurality of flexible, electrically conductive circuit traces (e.g., 710/712/714/716/718/720) is adhered. Two of these circuit traces 710 and 712 form a segment of the power distribution bus, and another two of these circuit traces 714 and 716 form a segment of the serial communication bus. In an exemplary version of this implementation copper ripstop fabric is used for each of the circuit traces 710/712/714/716/718/720, and either conventional felt or conventional cotton canvas is used for the base material 708. It will be appreciated that the heating cell can be fabricated using various methods. In an exemplary version of this implementation the heating cell is fabricated as follows. The circuit traces are first adhered in a prescribed pattern to the front and rear of a large section of the base material 708, and the heating cell is then raster cut out of this large section. Then, the microcontroller 700 and wires (e.g., 722) emanating from the battery 702 are electrically secured (using the conductive adhesive transfer tape) to appropriate locations on the circuit traces on the front of the base material 708, and the two ends of the resistive wire 704 are similarly electrically secured to the circuit traces 718 and 720 on the rear of the base material.

It is noted that the other types of actuation cells described herein employ soft circuits that are implemented in a manner that is generally similar to the just-described soft circuits for the vibration and heating cells.

Figure 9:
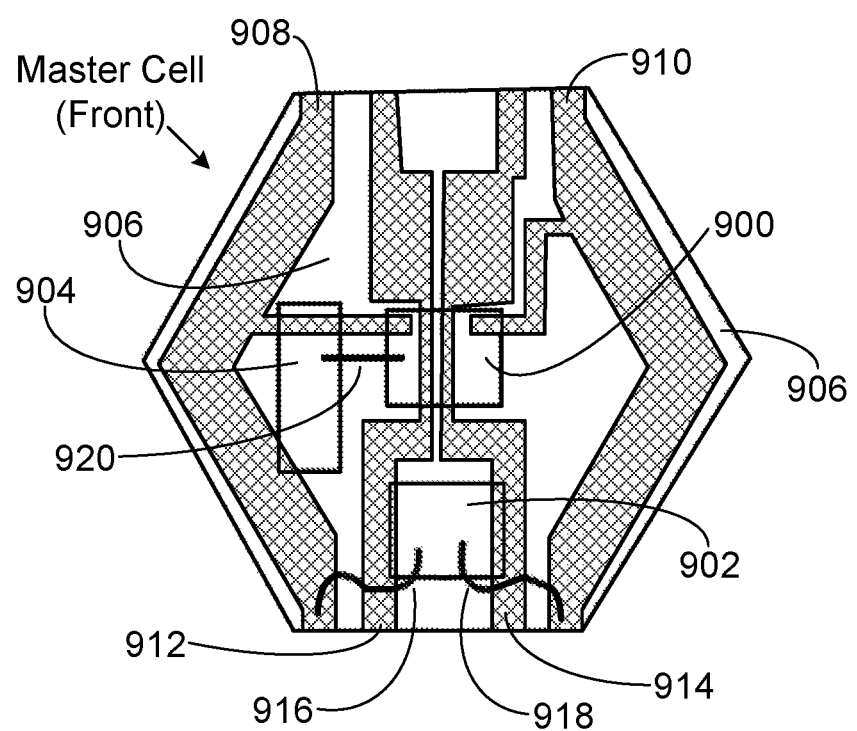
FIG. 9 is a diagram illustrating a front-side plan view of an exemplary implementation, in simplified form, of a soft circuit for the master cell.

FIG. 9 illustrates a front-side plan view of an exemplary implementation, in simplified form, of a soft circuit for the master cell. As exemplified in FIG. 9, the soft circuit for the master cell includes a master microcontroller 900, a master battery 902, a wireless receiver 904, and a flexible, electrically non-conductive base material 906 onto which a plurality of flexible, electrically conductive circuit traces (e.g., 908/910/912/914) is adhered. Two of these circuit traces 908 and 910 form a segment of the power distribution bus, and another two of these circuit traces 912 and 914 form a segment of the serial communication bus. In an exemplary version of this implementation conventional copper ripstop fabric is used for each of the circuit traces 908/910/912/914, and either conventional felt or conventional cotton canvas is used for the base material 906. It will be appreciated that the master cell can be fabricated using various methods. In an exemplary version of this implementation the master cell is fabricated as follows. The circuit traces 908/910/912/914 are first adhered in a prescribed pattern to the front of a large section of the base material 906, and the master cell is then raster cut out of this large section. Then, the microcontroller 900 and wires (e.g., 916/918/920) emanating from the battery 902 and wireless receiver 904 are electrically secured (using the conductive adhesive transfer) to appropriate locations on the circuit traces, and the battery and wireless receiver are secured to appropriate locations on the front of the base material 906.

Figure 8:
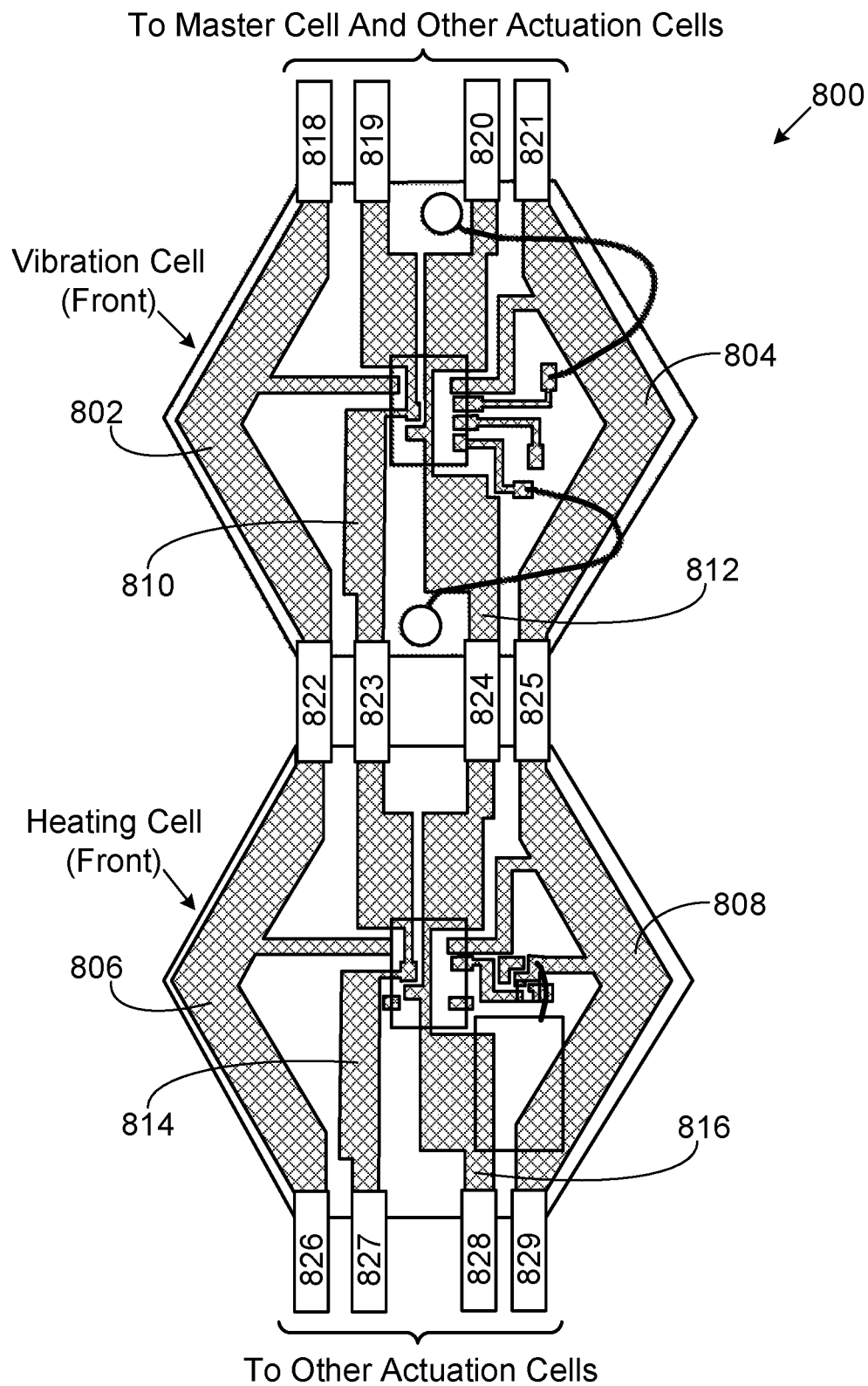
FIG. 8 is a diagram illustrating a front-side plan view of an exemplary implementation, in simplified form, of a chain of soft circuit cells and a method for electrically interconnecting the cells in the chain.

FIG. 8 illustrates a front-side plan view of an exemplary implementation, in simplified form, of a chain of soft circuit cells and a method for electrically interconnecting the cells in the chain. As exemplified in FIG. 8, the chain 800 includes a master cell (not shown), a vibration cell, a heating cell, and other actuation cells (not shown). One of the circuit traces 802 that forms a segment of the power distribution bus on the vibration cell is electrically connected to the corresponding power distribution bus circuit trace (not shown) on the soft circuit cell that immediately precedes the vibration cell in the chain 800 (hereafter simply referred to as the immediately preceding cell) by a flexible electrical connector 818, and is also electrically connected to the corresponding power distribution bus circuit trace 806 on the heating cell by another flexible electrical connector 822. The circuit trace 806 is also electrically connected to the corresponding power distribution bus circuit trace (not shown) on the soft circuit cell that immediately follows the heating cell in the chain 800 (hereafter simply referred to as the immediately following cell) by another flexible electrical connector 826. The other of the circuit traces 804 that forms a segment of the power distribution bus on the vibration cell is electrically connected to the corresponding power distribution bus circuit trace (not shown) on the immediately preceding cell by another flexible electrical connector 821, and is also electrically connected to the corresponding power distribution bus circuit trace 808 on the heating cell by another flexible electrical connector 825. The circuit trace 808 is also electrically connected to the corresponding power distribution bus circuit trace (not shown) on the immediately following cell by another flexible electrical connector 829. One of the circuit traces 810 that forms a segment of the serial communication bus on the vibration cell is electrically connected to the corresponding serial communication bus circuit trace (not shown) on the immediately preceding cell by another flexible electrical connector 819, and is also electrically connected to the corresponding serial communication bus circuit trace 814 on the heating cell by another flexible electrical connector 823. The circuit trace 814 is also electrically connected to the corresponding serial communication bus circuit trace (not shown) on the immediately following cell by another flexible electrical connector 827. The other of the circuit traces 812 that forms a segment of the serial communication bus on the vibration cell is electrically connected to the corresponding serial communication bus circuit trace (not shown) on the immediately preceding cell by another flexible electrical connector 820, and is also electrically connected to the corresponding serial communication bus circuit trace 816 on the heating cell by another flexible electrical connector 824. The circuit trace 816 is also electrically connected to the corresponding serial communication bus circuit trace (not shown) on the immediately following cell by another flexible electrical connector 828. In an exemplary version of this implementation conventional, electrically conductive VELCRO® (a registered trademark of Velcro Industries) is used for the just-described flexible electrical connectors 818-829.

2.5 Wearable Device Form Factors

As stated heretofore and as will be described in more detail hereafter, the wearable device implementations described herein are lightweight, supple and comfortable. The wearable device implementations also employ a modular, soft-circuit-based design that allows the wearable device implementations to be realized in a wide variety of garment form factors that look fashionable, blend in with the latest fashion trends, can be discreetly worn as an everyday garment by many types of users, and can be individually customized to meet the specific personal needs and preferences of many types of users. For example, a given user can specify the type of garment they prefer, the types and quantities of actuation cells they prefer, and their preference as to where to place each of the actuation cells in the garment. The master and actuation cells can generally have any prescribed shape and size, or a combination of different shapes and sizes. In an exemplary implementation of the wearable device the master and actuation cells each have a hexagonal shape. The hexagonal shape is advantageous in that it adds visual appeal to the garment and facilitates the realization of many different garment form factors.

Figure 10:
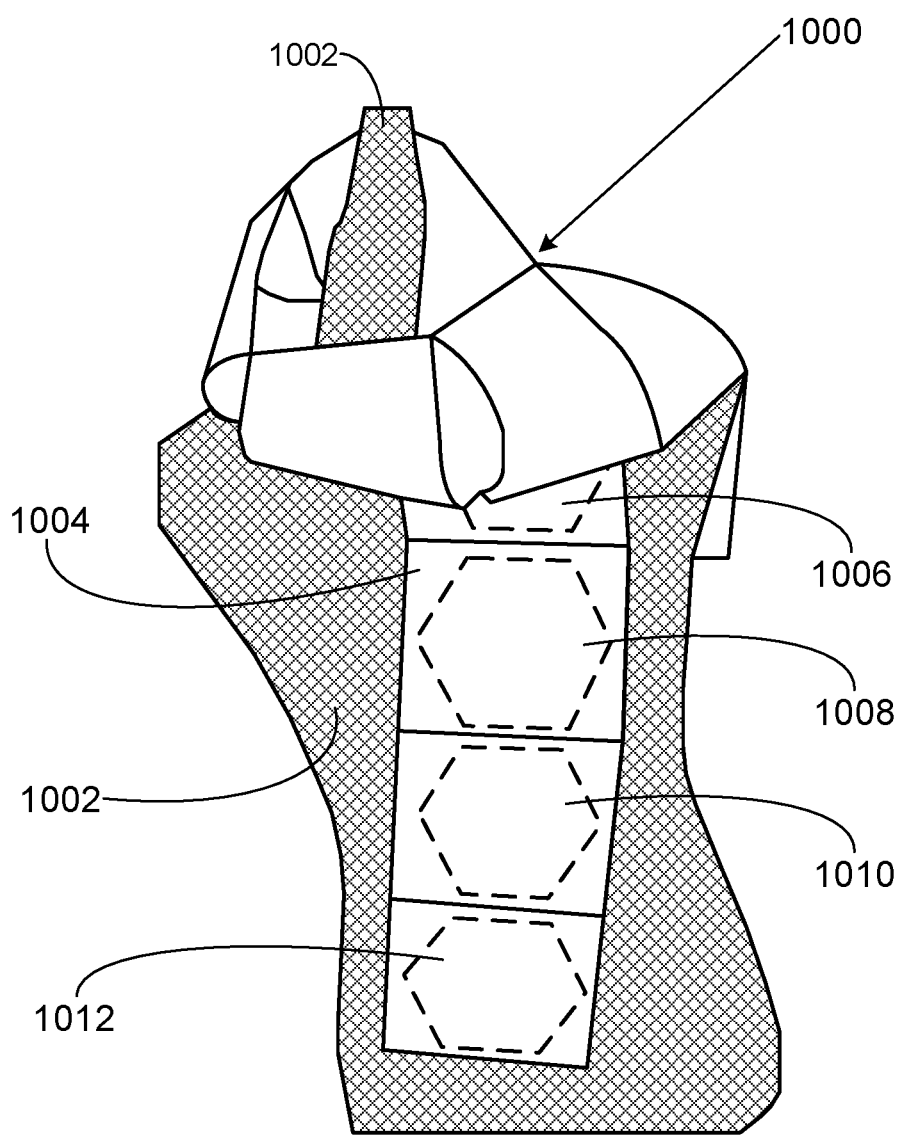
FIG. 10 is a greyscale image illustrating a scarf implementation of the wearable device described herein.

FIG. 10 illustrates a scarf implementation of the wearable device described herein. As exemplified in FIG. 10, a master cell (e.g., 1012) and eleven actuation cells (e.g., 1006/1008/1010) are physically interconnected in series to form a scarf 1000 that is being worn by a user 1002, where the master and each of the actuations cells include an electrically non-conductive fabric covering (e.g., 1004). As further exemplified in FIG. 10, the scarf 1000 has a width and length that are similar to the width and length of a typical conventional scarf, and can be wrapped around the user 1002 in a vest-like manner if such comfort is desired by the user. The scarf 1000 is also quite versatile in that it can be folded and worn by the user 1002 in a vast number of ways in addition to that which is shown in FIG. 10. For example, in the case where the scarf 1000 includes one or more lighting cells and the user 1002 does not want the lighting actuations of these cells to be visible to other people, the user can drape the scarf around their head in a hood-like manner with the light output elements facing inward. It is noted that in addition to the just-described scarf implementation, many other garment form factor implementations of the wearable device are also possible including, but not limited to, a vest and a belt.

2.6 Wearable Device Fabric Covering

Referring again to FIG. 3, the electrically non-conductive fabric covering 326 around the master cell 302 and the electrically non-conductive fabric coverings 328 and 330 around the actuation cells 310 and 318 can be realized in various ways. For example, in one implementation of the wearable device these fabric coverings are implemented as separate fabric modules that are physically interconnected to form a prescribed type of garment, where each of the fabric modules has a pocket into which either the master cell or one of the actuation cells is disposed. In another implementation of the wearable device these fabric coverings are implemented as a single fabric module into which the physically interconnected master and actuation cells are disposed.

It will be appreciated that various types of fabric can be used for the electrically non-conductive fabric coverings. In an exemplary implementation of the wearable device described herein woven cotton is used for these fabric coverings. Woven cotton is advantageous in that it is soft, lightweight, and breathable, thus allowing heat generated by the master and actuation cells to dissipate easily. Woven cotton is also sturdy enough to house the cells, and it is available in a wide variety of visually appealing designs.

2.7 Process Framework

Figure 11:
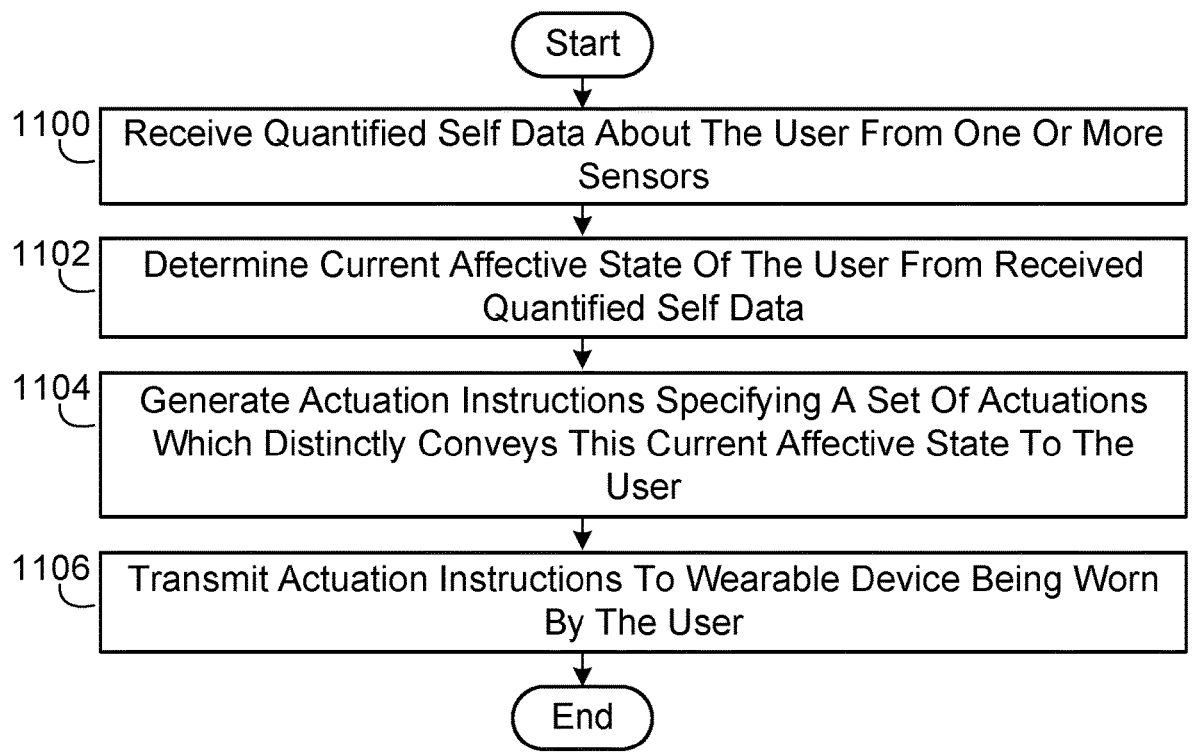
FIG. 11 is a flow diagram illustrating one implementation, in simplified form, of a process for conveying affective state information to a user.

FIG. 11 illustrates one implementation, in simplified form, of a process for conveying affective state information to a user. As will be appreciated from the more detailed description that follows and referring again to FIG. 1, the process implementation illustrated in FIG. 11 is based on the system framework 100 implementation illustrated in FIG. 1 and described heretofore. As exemplified in FIG. 11, the process starts with the local computing device that is in the vicinity of the user receiving quantified self data about the user from one or more sensors (process action 1100). These sensors can be any of the sensors that are physically attached to the body of the user, or any of the sensors that are remote from but in the immediate vicinity of the user, or any of the devices that the user has occasion to come in physical contact with, or any combination thereof. The local computing device then determines the current affective state of the user from the received quantified self data (process action 1102). As is appreciated in the art of affective computing, this determination can be made using various conventional machine learning methods (such as linear regression, among others) to analyze the received quantified self data. The processing performed in process action 1102 has the technical effect of converting the quantified self data about the user into the current affective state of the user. The local computing device then generates actuation instructions that specify a set of actuations which distinctly conveys this current affective state to the user (process action 1104). The local computing device then transmits these actuation instructions to the wearable device that is being worn by the user (process action 1106).

Figure 12:
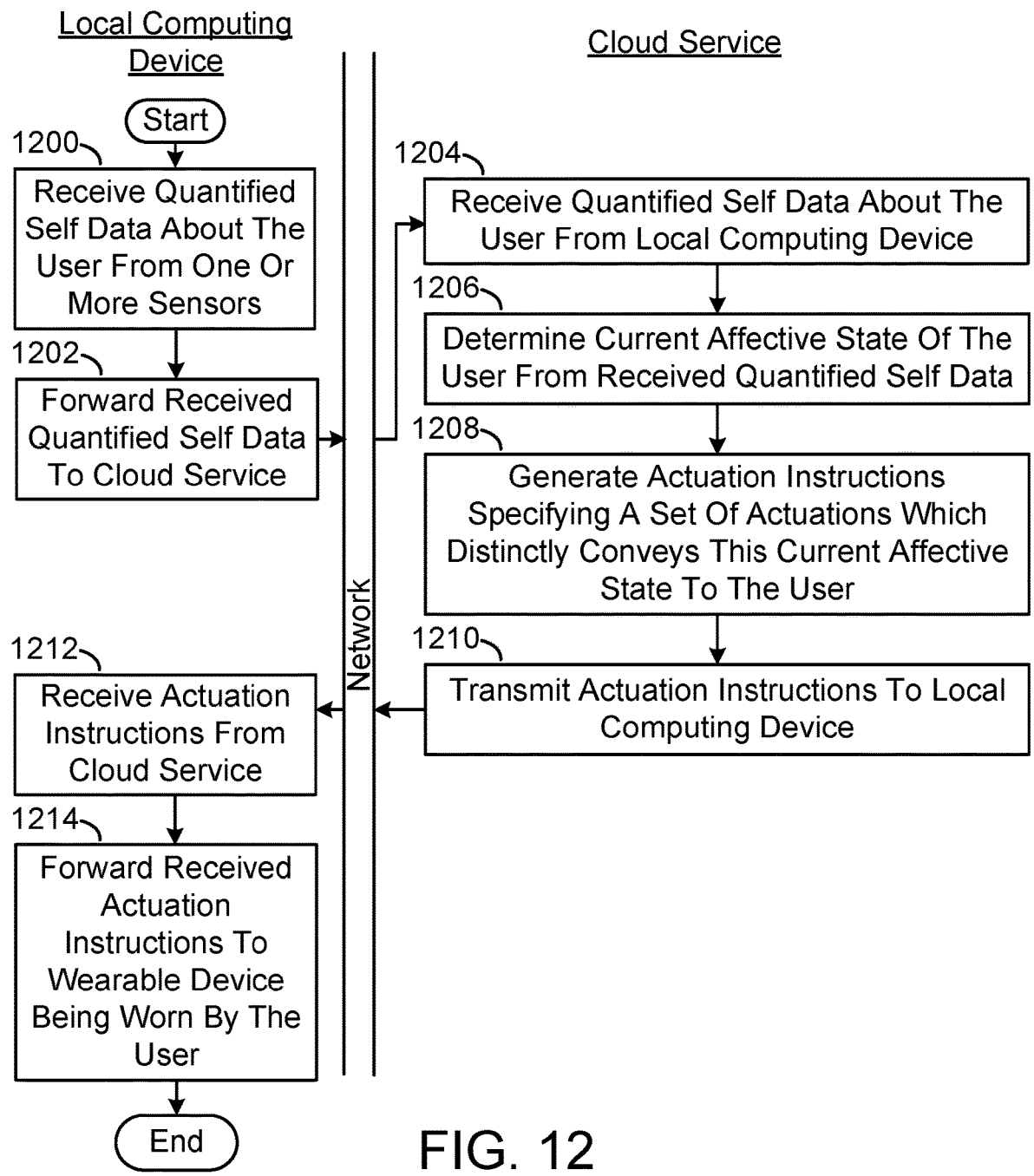
FIG. 12 is a flow diagram illustrating another implementation, in simplified form, of a process for conveying affective state information to a user.

FIG. 12 illustrates another implementation, in simplified form, of a process for conveying affective state information to a user. As will be appreciated from the more detailed description that follows and referring again to FIG. 2, the process implementation illustrated in FIG. 12 is based on the system framework 200 implementation illustrated in FIG. 2 and described heretofore. As exemplified in FIG. 12, the process starts with the local computing device that is in the vicinity of the user receiving quantified self data about the user from one or more of the just-described sensors (process action 1200). The local computing device then forwards the received quantified self data to the aforementioned cloud service (process action 1202). Upon receiving the quantified self data forwarded from the local computing device (process action 1204), the cloud service determines the current affective state of the user from the received quantified self data (process action 1206), where this determination can be made using the just-described machine learning methods. The processing performed in process action 1206 has the technical effect of converting the quantified self data about the user into the current affective state of the user. The cloud service then generates actuation instructions that specify a set of actuations which distinctly conveys this current affective state to the user (process action 1208), and transmits these actuation instructions to the local computing device (process action 1210). Upon receiving the actuation instructions transmitted from the cloud service (process action 1212), the local computing device forwards them to the wearable device that is being worn by the user (process action 1214).

3.0 Other Implementations

While the wearable device has been described by specific reference to implementations thereof, it is understood that variations and modifications thereof can be made without departing from the true spirit and scope of the wearable device. By way of example but not limitation, in addition to conveying the current affective state of the user to the user, an alternate implementation of the wearable device is possible where the wearable device conveys the current affective state of one or more other people, either individually or in aggregate, who are located in the vicinity of the user to the user. In other words, the actuation instructions that are received by the master cell of the wearable device may specify one or more actuations which distinctly convey the current affective state of these other people. This alternate implementation thus allows the user to reflect on and react to the current affective state of these other people, and informs the user when and how the affective state of these other people changes. For example, in a situation where a user is about to enter a conference room where a meeting is taking place, the wearable device being worn by the user can receive actuation instructions that cause the wearable device to generate a prescribed set of actuations which distinctly convey the current affective state of the people in the conference room. The wearable device can optionally also include one or more fabric modules each having a pocket into which either additional user electronics, or stress relief balls, or weights, or other items may be disposed. The stress relief balls may be squeezed by the user when they are stressed, thus serving to further reduce their stress level. The weights may serve to further reduce the stress level of an autistic user. Small balloons filled with either sand or a gel substance may serve as both weights and stress relief balls.

Additionally, rather than the electrical connection between each of the actuation cells and the master cell including a power distribution bus that supplies power from the master battery on the master cell to each of the actuation cells, an alternate implementation of the wearable device is possible where each of the actuation cells has its own battery. An alternate implementation of the audio cell is also possible where the audio cell includes a wireless transmitter (such as a conventional Bluetooth transmitter module, or the like) that is configured to allow the audio cell to be paired with (e.g., wirelessly coupled to) a hearing aid that may be worn by a hearing impaired user, and transmit the audio actuation generated by the audio cell to the hearing aid. An alternate implementation of the wearable device is also possible where the wearable device includes a plurality of master cells each of which is electrically connected to and controls a different group of actuation cells. Furthermore, rather than each of the actuation cells being electrically connected to the master cell, another alternate implementation of the wearable device is possible where each of the actuation cells is wirelessly connected to the master cell in a manner that allows the master cell to wirelessly transmit the activation and deactivation commands to each of the activation cells, and also allows the master cell to wirelessly transmit power to each of the activation cells.

It is noted that any or all of the aforementioned implementations throughout the description may be used in any combination desired to form additional hybrid implementations. In addition, although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What has been described above includes example implementations. It is, of course, not possible to describe every conceivable combination of components or methodologies for purposes of describing the claimed subject matter, but one of ordinary skill in the art may recognize that many further combinations and permutations are possible. Accordingly, the claimed subject matter is intended to embrace all such alterations, modifications, and variations that fall within the spirit and scope of the appended claims.

In regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the foregoing implementations include a system as well as a computer-readable storage media having computer-executable instructions for performing the acts and/or events of the various methods of the claimed subject matter.

There are multiple ways of realizing the foregoing implementations (such as an appropriate application programming interface (API), tool kit, driver code, operating system, control, standalone or downloadable software object, or the like), which enable applications and services to use the implementations described herein. The claimed subject matter contemplates this use from the standpoint of an API (or other software object), as well as from the standpoint of a software or hardware object that operates according to the implementations set forth herein. Thus, various implementations described herein may have aspects that are wholly in hardware, or partly in hardware and partly in software, or wholly in software.

The aforementioned systems have been described with respect to interaction between several components. It will be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (e.g., hierarchical components).

Additionally, it is noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

4.0 Exemplary Operating Environments

Figure 13:
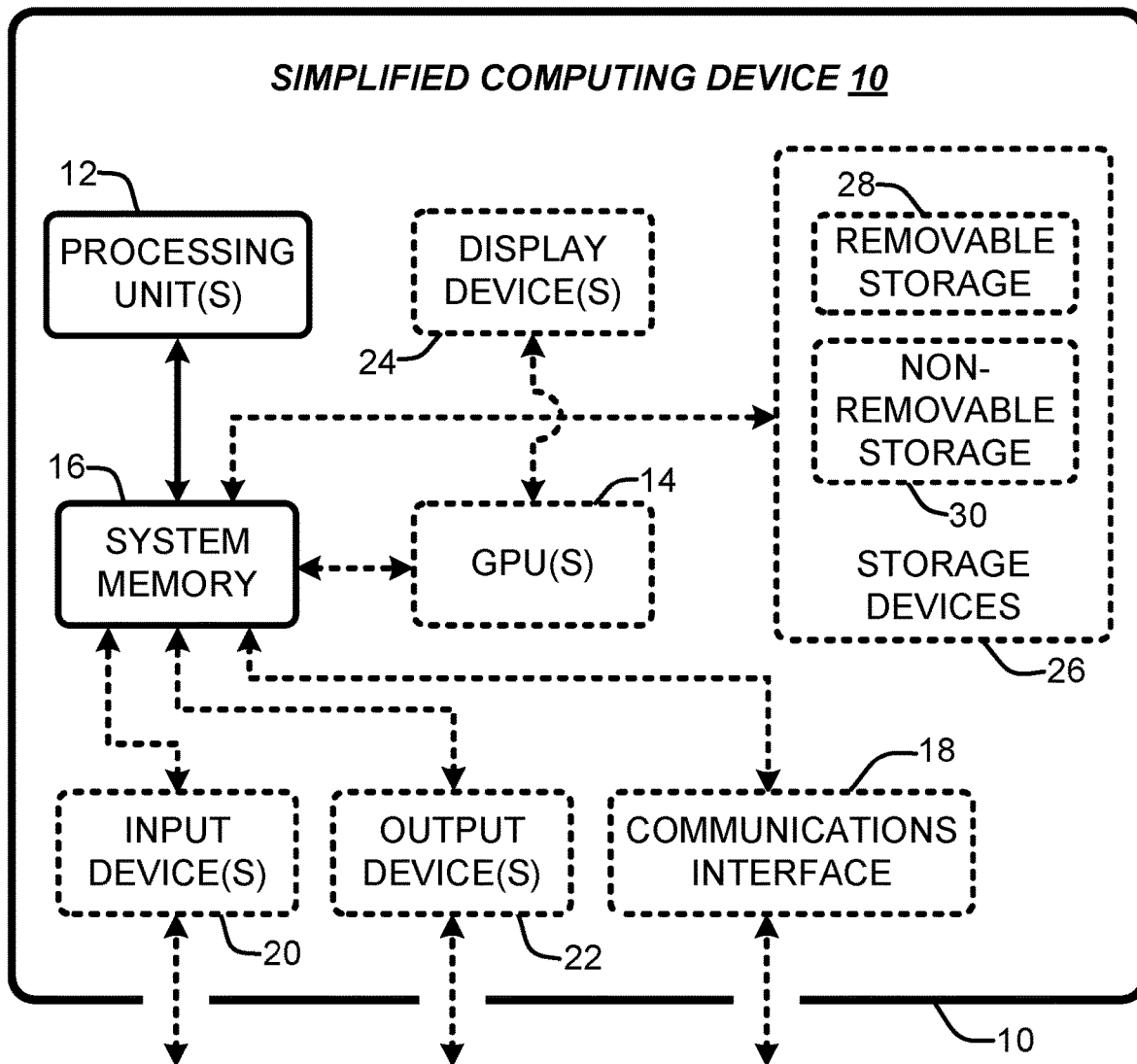
FIG. 13 is a diagram illustrating a simplified example of a general-purpose computer system on which various portions and elements of the wearable device implementations described herein may be realized.

The wearable device implementations described herein are operational within numerous types of general purpose or special purpose computing system environments or configurations. FIG. 13 illustrates a simplified example of a general-purpose computer system on which various implementations and elements of the wearable device, as described herein, may be implemented. It is noted that any boxes that are represented by broken or dashed lines in the simplified computing device 10 shown in FIG. 13 represent alternate implementations of the simplified computing device. As described below, any or all of these alternate implementations may be used in combination with other alternate implementations that are described throughout this document. The simplified computing device 10 is typically found in devices having at least some minimum computational capability such as personal computers (PCs), server computers, handheld computing devices, laptop or mobile computers, communications devices such as cell phones and personal digital assistants (PDAs), multiprocessor systems, microprocessor-based systems, set top boxes, programmable consumer electronics, network PCs, minicomputers, mainframe computers, and audio or video media players.

To allow a device to realize the wearable device implementations described herein, the device should have a sufficient computational capability and system memory to enable basic computational operations. In particular, the computational capability of the simplified computing device 10 shown in FIG. 13 is generally illustrated by one or more processing unit(s) 12, and may also include one or more graphics processing units (GPUs) 14, either or both in communication with system memory 16. Note that that the processing unit(s) 12 of the simplified computing device 10 may be specialized microprocessors (such as a digital signal processor (DSP), a very long instruction word (VLIW) processor, a field-programmable gate array (FPGA), or other micro-controller) or can be conventional central processing units (CPUs) having one or more processing cores.

In addition, the simplified computing device 10 may also include other components, such as, for example, a communications interface 18. The simplified computing device 10 may also include one or more conventional computer input devices 20 (e.g., touchscreens, touch-sensitive surfaces, pointing devices, keyboards, audio input devices, voice or speech-based input and control devices, video input devices, haptic input devices, devices for receiving wired or wireless data transmissions, and the like) or any combination of such devices.

Similarly, various interactions with the simplified computing device 10 and with any other component or feature of the wearable device implementations described herein, including input, output, control, feedback, and response to one or more users or other devices or systems associated with the wearable device implementations, are enabled by a variety of Natural User Interface (NUI) scenarios. The NUI techniques and scenarios enabled by the wearable device implementations include, but are not limited to, interface technologies that allow one or more users user to interact with the wearable device implementations in a "natural" manner, free from artificial constraints imposed by input devices such as mice, keyboards, remote controls, and the like.

Such NUI implementations are enabled by the use of various techniques including, but not limited to, using NUI information derived from user speech or vocalizations captured via microphones or other sensors (e.g., speech and/or voice recognition). Such NUI implementations are also enabled by the use of various techniques including, but not limited to, information derived from a user's facial expressions and from the positions, motions, or orientations of a user's hands, fingers, wrists, arms, legs, body, head, eyes, and the like, where such information may be captured using various types of 2D or depth imaging devices such as stereoscopic or time-of-flight camera systems, infrared camera systems, RGB (red, green and blue) camera systems, and the like, or any combination of such devices. Further examples of such NUI implementations include, but are not limited to, NUI information derived from touch and stylus recognition, gesture recognition (both onscreen and adjacent to the screen or display surface), air or contact-based gestures, user touch (on various surfaces, objects or other users), hover-based inputs or actions, and the like. Such NUI implementations may also include, but are not limited, the use of various predictive machine intelligence processes that evaluate current or past user behaviors, inputs, actions, etc., either alone or in combination with other NUI information, to predict information such as user intentions, desires, and/or goals. Regardless of the type or source of the NUI-based information, such information may then be used to initiate, terminate, or otherwise control or interact with one or more inputs, outputs, actions, or functional features of the wearable device implementations described herein.

However, it should be understood that the aforementioned exemplary NUI scenarios may be further augmented by combining the use of artificial constraints or additional signals with any combination of NUI inputs. Such artificial constraints or additional signals may be imposed or generated by input devices such as mice, keyboards, and remote controls, or by a variety of remote or user worn devices such as accelerometers, electromyography (EMG) sensors for receiving myoelectric signals representative of electrical signals generated by user's muscles, heart-rate monitors, galvanic skin conduction sensors for measuring user perspiration, wearable or remote biosensors for measuring or otherwise sensing user brain activity or electric fields, wearable or remote biosensors for measuring user body temperature changes or differentials, and the like. Any such information derived from these types of artificial constraints or additional signals may be combined with any one or more NUI inputs to initiate, terminate, or otherwise control or interact with one or more inputs, outputs, actions, or functional features of the wearable device implementations described herein.

The simplified computing device 10 may also include other optional components such as one or more conventional computer output devices 22 (e.g., display device(s) 24, audio output devices, video output devices, devices for transmitting wired or wireless data transmissions, and the like). Note that typical communications interfaces 18, input devices 20, output devices 22, and storage devices 26 for general-purpose computers are well known to those skilled in the art, and will not be described in detail herein.

The simplified computing device 10 shown in FIG. 13 may also include a variety of computer-readable media. Computer-readable media can be any available media that can be accessed by the computer 10 via storage devices 26, and can include both volatile and nonvolatile media that is either removable 28 and/or non-removable 30, for storage of information such as computer-readable or computer-executable instructions, data structures, program modules, or other data. Computer-readable media includes computer storage media and communication media. Computer storage media refers to tangible computer-readable or machine-readable media or storage devices such as digital versatile disks (DVDs), blu-ray discs (BD), compact discs (CDs), floppy disks, tape drives, hard drives, optical drives, solid state memory devices, random access memory (RAM), read-only memory (ROM), electrically erasable programmable read-only memory (EEPROM), CD-ROM or other optical disk storage, smart cards, flash memory (e.g., card, stick, and key drive), magnetic cassettes, magnetic tapes, magnetic disk storage, magnetic strips, or other magnetic storage devices. Further, a propagated signal is not included within the scope of computer-readable storage media.

Retention of information such as computer-readable or computer-executable instructions, data structures, program modules, and the like, can also be accomplished by using any of a variety of the aforementioned communication media (as opposed to computer storage media) to encode one or more modulated data signals or carrier waves, or other transport mechanisms or communications protocols, and can include any wired or wireless information delivery mechanism. Note that the terms "modulated data signal" or "carrier wave" generally refer to a signal that has one or more of its characteristics set or changed in such a manner as to encode information in the signal. For example, communication media can include wired media such as a wired network or direct-wired connection carrying one or more modulated data signals, and wireless media such as acoustic, radio frequency (RF), infrared, laser, and other wireless media for transmitting and/or receiving one or more modulated data signals or carrier waves.

Furthermore, software, programs, and/or computer program products embodying some or all of the various wearable device implementations described herein, or portions thereof, may be stored, received, transmitted, or read from any desired combination of computer-readable or machine-readable media or storage devices and communication media in the form of computer-executable instructions or other data structures. Additionally, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, or media.

The wearable device implementations described herein may be further described in the general context of computer-executable instructions, such as program modules, being executed by a computing device. Generally, program modules include routines, programs, objects, components, data structures, and the like, that perform particular tasks or implement particular abstract data types. The wearable device implementations may also be practiced in distributed computing environments where tasks are performed by one or more remote processing devices, or within a cloud of one or more devices, that are linked through one or more communications networks. In a distributed computing environment, program modules may be located in both local and remote computer storage media including media storage devices. Additionally, the aforementioned instructions may be implemented, in part or in whole, as hardware logic circuits, which may or may not include a processor.

Alternatively, or in addition, the functionality described herein can be performed, at least in part, by one or more hardware logic components. For example, and without limitation, illustrative types of hardware logic components that can be used include FPGAs, application-specific integrated circuits (ASICs), application-specific standard products (ASSPs), system-on-a-chip systems (SOCs), complex programmable logic devices (CPLDs), and so on.

5.0 Claim Support and Further Implementations

The following paragraphs summarize various examples of implementations which may be claimed in the present document. However, it should be understood that the implementations summarized below are not intended to limit the subject matter which may be claimed in view of the foregoing descriptions. Further, any or all of the implementations summarized below may be claimed in any desired combination with some or all of the implementations described throughout the foregoing description and any implementations illustrated in one or more of the figures, and any other implementations described below. In addition, it should be noted that the following implementations are intended to be understood in view of the foregoing description and figures described throughout this document.

In one implementation, a wearable device for conveying information to a user includes a master soft circuit cell and a plurality of actuation soft circuit cells. The master and actuation soft circuit cells are physically interconnected to form a garment being worn by the user. The master soft circuit cell and each of the actuation soft circuit cells include an electrically non-conductive fabric covering. Each of the actuation soft circuit cells are electrically connected to and operate under the control of the master soft circuit cell. The master soft circuit cell is configured to wirelessly receive actuation instructions and activate a combination of the actuation soft circuit cells based on the received actuation instructions. Each of the actuation soft circuit cells is configured to generate a particular actuation that is perceived by one or more senses of the user whenever the actuation soft circuit cell is activated by the master soft circuit cell.

In one implementation, the master soft circuit cell further includes a battery, a microcontroller, and a wireless receiver. The electrical connection between each of the actuation soft circuit cells and the master soft circuit cell includes a power distribution bus and a communication bus that serially pass through the master and actuation soft circuit cells. The received actuation instructions specify a set of actuations. The power distribution bus is configured to supply power from the battery to each of the actuation soft circuit cells. The microcontroller is configured to interpret the received actuation instructions and send commands over the communication bus to each of the actuation soft circuit cells, the commands causing the actuation soft circuit cells whose particular actuation is in the set to be activated, and causing the actuation soft circuit cells whose particular actuation is not in the set to be deactivated. In one version of this implementation, the wireless receiver includes one of a Bluetooth personal area network receiver; or a Wi-Fi local area network receiver. In another version, the communication bus includes an Inter-Integrated Circuit (I2C) bus and the commands follow the I2C message protocol.

In one implementation, each of the actuation soft circuit cells further includes a microcontroller and an actuator unit. The electrical connection between each of the actuation soft circuit cells and the master soft circuit cell includes a power distribution bus and a communication bus that serially pass through the master and actuation soft circuit cells. Each of the actuation soft circuit cells is configured to receive power from the master soft circuit cell over the power distribution bus. The microcontroller on each of the actuation soft circuit cells is configured to receive commands from the master soft circuit cell over the communication bus, and either turn on or turn off the actuator unit on the actuation soft circuit cell based on the received commands. In one version of this implementation, the actuator unit on one or more of the actuation soft circuit cells includes one of a heating element that when turned on generates heat; or a cooling element that when turned on removes heat from the body of the user; or an audio output element that when turned on plays a desired one of a plurality of different sounds; or a vibration element that when turned on vibrates; or a light output element that when turned on displays a desired one of a plurality of different lighting effects; or a pressure producing element that when turned on applies pressure to the body of the user; or a shape changing element that when turned on changes the physical shape of the one or more actuation soft circuit cells.

In one implementation, the information being conveyed to the user includes the current affective state of the user, and the received actuation instructions specify a set of actuations which distinctly conveys the current affective state to the user. In one version of this implementation, whenever the current affective state of the user is stressed the set of actuations includes a short sequence of vibration pulses followed by removing heat from the body of the user, playing a soothing and slow type of music, and applying pressure to the body of the user. Whenever the current affective state of the user is sad the set of actuations includes a short sequence of vibration pulses followed by applying heat to the body of the user, playing a cheerful and upbeat type of music, and displaying a soothing type of lighting effect. Whenever the current affective state of the user is calm the set of actuations includes a short sequence of vibration pulses. Whenever the current affective state of the user is happy the set of actuations includes a short sequence of vibration pulses followed by playing a cheerful and upbeat type of music, and displaying a soothing type of lighting effect. Whenever the current affective state of the user is excited the set of actuations includes a short sequence of vibration pulses followed by removing heat from the body of the user, playing a cheerful and upbeat type of music, and displaying a festive type of lighting effect. In another version, whenever the current affective state of the user is stressed the set of actuations includes a short sequence of vibration pulses followed by applying heat to the body of the user, playing a soothing and slow type of music, and applying pressure to the body of the user. Whenever the current affective state of the user is sad the set of actuations includes a short sequence of vibration pulses followed by applying heat to the body of the user, and playing a cheerful and upbeat type of music. Whenever the current affective state of the user is calm the set of actuations includes a short sequence of vibration pulses. Whenever the current affective state of the user is happy the set of actuations includes a short sequence of vibration pulses followed by playing a cheerful and upbeat type of music. Whenever the current affective state of the user is excited the set of actuations includes a short sequence of vibration pulses followed by playing a cheerful and upbeat type of music.

In one implementation, the actuation soft circuit cells include at least one of a heating cell configured to generate a heating actuation that warms the user whenever the heating cell is activated by the master soft circuit cell; or a cooling cell configured to generate a cooling actuation that cools the user whenever the cooling cell is activated by the master soft circuit cell; or an audio cell configured to generate an audio actuation that may be heard and felt by the user whenever the audio cell is activated by the master soft circuit cell; or a vibration cell configured to generate a vibration actuation that may be felt by the user whenever the vibration cell is activated by the master soft circuit cell; or a lighting cell configured to generate a lighting actuation that may be seen by the user whenever the lighting cell is activated by the master soft circuit cell; or a pressure cell configured to generate a pressure actuation that may be felt by the user whenever the pressure cell is activated by the master soft circuit cell; or a rubbing cell configured to generate a rubbing actuation that may be felt by the user whenever the rubbing cell is activated by the master soft circuit cell. In one version of this implementation, the audio cell includes a wireless transmitter configured to transmit the audio actuation to a hearing aid being worn by the user.

In one implementation, the master soft circuit cell and each of the actuation soft circuit cells further include a flexible, electrically non-conductive base material; and a plurality of flexible, electrically conductive circuit traces adhered to the base material in a prescribed pattern. In one version of this implementation, the base material includes one of felt; or cotton canvas. In another version, each of the circuit traces includes copper ripstop fabric. In another implementation, the above-mentioned garment includes one of a scarf; or a vest; or a belt.

The implementations and versions described in any of the previous paragraphs in this section may also be combined with each other, and with one or more of the implementations and versions described prior to this section. For example, some or all of the preceding implementations and versions may be combined with the foregoing implementation where the information being conveyed to the user includes the current affective state of the user, and the received actuation instructions specify a set of actuations which distinctly conveys the current affective state to the user. In addition, some or all of the preceding implementations and versions may be combined with the foregoing implementation where the actuation soft circuit cells include at least one of a heating cell configured to generate a heating actuation that warms the user whenever the heating cell is activated by the master soft circuit cell; or a cooling cell configured to generate a cooling actuation that cools the user whenever the cooling cell is activated by the master soft circuit cell; or an audio cell configured to generate an audio actuation that may be heard and felt by the user whenever the audio cell is activated by the master soft circuit cell; or a vibration cell configured to generate a vibration actuation that may be felt by the user whenever the vibration cell is activated by the master soft circuit cell; or a lighting cell configured to generate a lighting actuation that may be seen by the user whenever the lighting cell is activated by the master soft circuit cell; or a pressure cell configured to generate a pressure actuation that may be felt by the user whenever the pressure cell is activated by the master soft circuit cell; or a rubbing cell configured to generate a rubbing actuation that may be felt by the user whenever the rubbing cell is activated by the master soft circuit cell. In addition, some or all of the preceding implementations and versions may be combined with the foregoing implementation where the master soft circuit cell and each of the actuation soft circuit cells further include a flexible, electrically non-conductive base material; and a plurality of flexible, electrically conductive circuit traces adhered to the base material in a prescribed pattern.

In one implementation, a system for conveying affective state information to a user includes a computing device and a computer program having program modules executable by the computing device. The computing device is directed by the program modules of the computer program to receive quantified self data about the user from one or more sensors; determine the current affective state of the user from the quantified self data; generate actuation instructions specifying a set of actuations which distinctly conveys the current affective state to the user; and transmit the actuation instructions to a wearable device being worn by the user.

In one implementation of the just-described system, the quantified self data includes one or more of data about the physiology of the user; or data about the activities of the user. In another implementation, whenever the current affective state of the user is stressed the set of actuations includes a short sequence of vibration pulses followed by removing heat from the body of the user, playing a soothing and slow type of music, and applying pressure to the body of the user. Whenever the current affective state of the user is sad the set of actuations includes a short sequence of vibration pulses followed by applying heat to the body of the user, playing a cheerful and upbeat type of music, and displaying a soothing type of lighting effect. Whenever the current affective state of the user is calm the set of actuations includes a short sequence of vibration pulses. Whenever the current affective state of the user is happy the set of actuations includes a short sequence of vibration pulses followed by playing a cheerful and upbeat type of music, and displaying a soothing type of lighting effect. Whenever the current affective state of the user is excited the set of actuations includes a short sequence of vibration pulses followed by removing heat from the body of the user, playing a cheerful and upbeat type of music, and displaying a festive type of lighting effect.

In one implementation, a system for conveying affective state information to a user includes one or more computing devices and a computer program having program modules executable by the computing devices, where the computing devices are in communication with each other via a computer network whenever there is a plurality of computing devices. The computing devices are directed by the program modules of the computer program to receive quantified self data about the user from another computing device located in the vicinity of the user; determine the current affective state of the user from the quantified self data; generate actuation instructions specifying a set of actuations which distinctly conveys the current affective state to the user; and transmit the actuation instructions to the other computing device.

In one implementation of the just-described system, whenever the current affective state of the user is stressed the set of actuations includes a short sequence of vibration pulses followed by applying heat to the body of the user, playing a soothing and slow type of music, and applying pressure to the body of the user. Whenever the current affective state of the user is sad the set of actuations includes a short sequence of vibration pulses followed by applying heat to the body of the user, and playing a cheerful and upbeat type of music. Whenever the current affective state of the user is calm the set of actuations includes a short sequence of vibration pulses. Whenever the current affective state of the user is happy the set of actuations includes a short sequence of vibration pulses followed by playing a cheerful and upbeat type of music. Whenever the current affective state of the user is excited the set of actuations includes a short sequence of vibration pulses followed by playing a cheerful and upbeat type of music.

In various implementations, a wearable device is implemented by a means for conveying information to a user. For example, in one implementation, the wearable device includes a plurality of actuation soft circuit cell means each of which generates a particular actuation that is perceived by one or more senses of the user whenever it is activated; and a master soft circuit cell means for wirelessly receiving actuation instructions and activating a combination of the actuation soft circuit cell means based on the received actuation instructions. The master and actuation soft circuit cell means are physically interconnected to form a garment being worn by the user. The master soft circuit cell means and each of the actuation soft circuit cell means include an electrically non-conductive fabric covering. Each of the actuation soft circuit cell means is electrically connected to and operates under the control of the master soft circuit cell means.

In various implementations, an information conveyance system is implemented by a means for conveying affective state information to a user. For example, in one implementation, the information conveyance system includes a computing device that includes a processor configured to execute a receiving step for receiving quantified self data about the user from one or more sensors, a determining step for determining the current affective state of the user from the quantified self data, a generating step for generating actuation instructions specifying a set of actuations which distinctly conveys the current affective state to the user, and a transmitting step for transmitting the actuation instructions to a wearable device being worn by the user. In another implementation, the information conveyance system includes one or more computing devices, the computing devices being in communication with each other via a computer network whenever there is a plurality of computing devices, the computing devices including processors configured to execute a receiving step for receiving quantified self data about the user from another computing device located in the vicinity of the user, a determining step for determining the current affective state of the user from the quantified self data, a generating step for generating actuation instructions specifying a set of actuations which distinctly conveys the current affective state to the user, and a transmitting step for transmitting the actuation instructions to the other computing device.

Wherefore, what is claimed is:

1. A system for conveying affective state information to a user, comprising:
   a computing device; and
   a computer program stored on the computing device having program modules executable by the computing device, the computing device being directed by the program modules of the computer program to:
      receive quantified self data about the user from one or more sensors,
      determine a current affective state of the user from said quantified self data,
      generate actuation instructions specifying a set of actuations which distinctly conveys said current affective state to the user, and
      transmit said actuation instructions to a wearable device being worn by the user.

2. The system of claim 1, wherein said quantified self data comprises one or more of:
   data about a physiology of the user; or
   data about activities of the user.

3. The system of claim 1, wherein, whenever the current affective state of the user is stressed said set of actuations comprises a short sequence of vibration pulses followed by removing heat from the body of the user, playing music of a subset of available audio, and applying pressure to the body of the user.

4. The system of claim 1, wherein, whenever the current affective state of the user is sad said set of actuations comprises a short sequence of vibration pulses followed by applying heat to the body of the user, playing music of a subset of the available audio, and displaying a lighting effect.

5. The system of claim 1, wherein, whenever the current affective state of the user is calm said set of actuations comprises a short sequence of vibration pulses.

6. The system of claim 1, wherein, whenever the current affective state of the user is happy said set of actuations comprises a short sequence of vibration pulses followed by playing music of a subset of available audio, and displaying a predetermined type of lighting effect.

7. The system of claim 6, wherein, whenever the current affective state of the user is excited said set of actuations comprises a short sequence of vibration pulses followed by removing heat from the body of the user, playing music of a subset of the available audio, and displaying a predetermined type of lighting effect.

8. A system for conveying affective state information to a user, comprising:
   one or more computing devices, said computing devices being in communication with each other via a computer network whenever there is a plurality of computing devices; and
   a computer program stored on the computing device having program modules executable by said computing devices, said computing devices being directed by the program modules of the computer program to,
      receive quantified self data about the user from another computing device located in the vicinity of the user,
      determine a current affective state of the user from said quantified self data,
      generate actuation instructions specifying a set of actuations which distinctly conveys said current affective state to the user, and
      transmit said actuation instructions to said other computing device.

9. The system of claim 8, wherein, whenever the current affective state of the user is stressed said set of actuations comprises a short sequence of vibration pulses followed by applying heat to the body of the user, playing music of a subset of available audio, and applying pressure to the body of the user.

10. The system of claim 8, wherein, whenever the current affective state of the user is sad said set of actuations comprises a short sequence of vibration pulses followed by applying heat to the body of the user, and playing music of a subset of available audio.

11. The system of claim 8, wherein, whenever the current affective state of the user is calm said set of actuations comprises a short sequence of vibration pulses.

12. The system of claim 8, wherein, whenever the current affective state of the user is happy said set of actuations comprises a short sequence of vibration pulses followed by playing music of a subset of available audio.

13. The system of claim 8, wherein, whenever the current affective state of the user is excited said set of actuations comprises a short sequence of vibration pulses followed by playing music of a subset of available audio.

14. A computer-implemented process for conveying affective state information to a user, the process comprising the actions of:
   using one or more computing devices to perform the following process actions, the computing devices being in communication with each other via a computer network whenever a plurality of computing devices is used:
      receiving quantified self data about the user from another computing device located in the vicinity of the user,
      determining a current affective state of the user from said quantified self data, generating actuation instructions specifying a set of actuations which distinctly conveys said current affective state to the user, and transmitting said actuation instructions to said other computing device.

15. The process of claim 14, wherein said quantified self data comprises one or more of:

data about a physiology of the user; or data about activities of the user.

16. The process of claim 14, wherein, whenever the current affective state of the user is stressed said set of actuations comprises a short sequence of vibration pulses followed by removing heat from the body of the user, playing music of a subset of available audio, and applying pressure to the body of the user.

17. The process of claim 14, wherein, whenever the current affective state of the user is sad said set of actuations comprises a short sequence of vibration pulses followed by applying heat to the body of the user, playing music of a subset of available audio, and displaying a predetermined type of lighting effect.

18. The process of claim 14, wherein, whenever the current affective state of the user is calm said set of actuations comprises a short sequence of vibration pulses.

19. The process of claim 14, wherein, whenever the current affective state of the user is happy said set of actuations comprises a short sequence of vibration pulses followed by playing music of a subset of available audio, and displaying a predetermined type of lighting effect.

20. The process of claim 14, wherein, whenever the current affective state of the user is excited said set of actuations comprises a short sequence of vibration pulses followed by removing heat from the body of the user, playing music of a subset of available audio, and displaying a predetermined type of lighting effect.

21. A system for conveying affective state information, comprising:

a computing device; and a computer program stored on the computing device having a plurality of sub-programs executable by said computing device, wherein the sub-programs configure said computing device to, receive quantified self data about a user from one or more sensors, determine a current affective state of the user from said quantified self data, generate affective state information which conveys said current affective state to the user, and output said affective state information.

22. The system of claim 21, wherein outputting said affective state information comprises outputting the affective state information to the user.

23. The system of claim 21, wherein outputting said affective state information comprises outputting the affective state information to a computing device.

24. A system for conveying affective state information, comprising:

an affective state information conveyor comprising one or more computing devices, said computing devices being in communication with each other via a computer network whenever there is a plurality of computing devices, and a computer program stored on the one or more computing devices having a plurality of sub-programs executable by said computing devices, wherein the sub-programs configure said computing devices to, receive quantified self data about a user from another computing device located in the vicinity of the user, determine a current affective state of the user from said quantified self data, generate affective state information which conveys said current affective state to the user, and output said affective state information.

25. The system of claim 24, wherein outputting said affective state information comprises outputting the affective state information to a computing device.

26. The system of claim 24, wherein outputting said affective state information comprises outputting the affective state information to the user via said other computing device located in the vicinity of the user.

* * * * *